(12) United States Patent
Latz et al.

(10) Patent No.: US 8,617,838 B2
(45) Date of Patent: Dec. 31, 2013

(54) FLUORESCENT PROTEINS AND RELATED METHODS AND COMPOUNDS

(75) Inventors: Eicke Latz, Worcester, MA (US); Brian G. Monks, Sudbury, MA (US); Douglas T. Golenbock, Wellesley, MA (US)

(73) Assignee: University of Massachusetts, Boston, MA (US)

(*) Notice: Subject to any disclaimer, the term of this patent is extended or adjusted under 35 U.S.C. 154(b) by 777 days.

(21) Appl. No.: 11/575,363

(22) PCT Filed: Sep. 20, 2005

(86) PCT No.: PCT/US2005/033778
§ 371 (c)(1),
(2), (4) Date: Jan. 29, 2008

(87) PCT Pub. No.: WO2006/101520
PCT Pub. Date: Sep. 28, 2006

(65) Prior Publication Data
US 2008/0261257 A1   Oct. 23, 2008

Related U.S. Application Data

(60) Provisional application No. 60/611,457, filed on Sep. 20, 2004.

(51) Int. Cl.
*C07K 1/00* (2006.01)
*C07K 4/00* (2006.01)
*C12Q 1/02* (2006.01)
*C12N 15/63* (2006.01)
*C12N 5/00* (2006.01)

(52) U.S. Cl.
USPC ............... 435/29; 436/8; 436/86; 435/320.1; 435/325; 536/23.1

(58) Field of Classification Search
None
See application file for complete search history.

(56) References Cited

U.S. PATENT DOCUMENTS 7,183,066 B2 * 2/2007 Fernandez-Salas et al. . 435/7.32
7,332,567 B2 * 2/2008 Steward et al. ............... 530/300

OTHER PUBLICATIONS

Imaging into the future: visualizing gene expression and protein interactions with fluorescent proteins Peter van Roessel Nature Cell Biology 4, E15-E20 (2002).*
Donnald Bennett et al Kinetic Characterizaation of the Interaction of Biotynylated Human Interleukin 5 with an Fc Chimera of its Receptor alpha Subunit and Development of an ELISA Sxreening Assay uding Real-Time Interaxtion Biosensor Analysis. Journal of Molecular recognition vol. 8, 53-58 (1995).*
Takaku Nagai et al a high-throughput method for development of FRET-based indicators for proteolysis Takeharu Nagai. Biochemical and Biophysical Research vol. 319, issue 1, p. 72-77, 2004.*
Anishetty et al. Tripeptide analysis of protein structures Biomed central Structural Biology, p. 1-8, Dec. 21, 2002.*
Alexander Domin et al Linked fluorophores FRET calibration and FRET studies of the Cyclin-CDK switch in mammalian cells. Confocal, Multiphoton, and Nonlinear Microscopic Imaging, Tony Wilson, editor, Proceedings of SPIE-OSA Biomedical Optics, SPIE vol. 5139 (2003).*
Nagy Peter et al. Novel calibration method for flow cytometric fluorescence resonance energy transfer measurements between visible fluorescent proteins. Cytometry A Oct. 2005;67(2):86-96.*
Campbell et al., "A monomeric red fluorescent protein," Proc. Natl. Acad. Sci. U.S.A. 99(12):7877-82 (2002).
Chudakov et al., "Kindling fluorescent proteins for precise in vivo photolabeling," Nat. Biotechnol. 21(2):191-194 (2003).
Chudakov et al., "Photoswitchable cyan fluorescent protein for protein tracking," Nat. Biotechnol. 22(11):1435-1439 (2004).
Clegg "Fluorescence resonance energy transfer," In: Fluorescence Imaging Spectroscopy and Microscopy, Wang and Herman, Eds., Wiley, New York, 137:179-251 (1996).
Gurskaya et al., "A colourless green fluorescent protein homologue from the non-fluorescent hydromedusa aequorea coerulescens and its fluorescent mutants," Biochem. J. 373(Pt. 2):403-408 (2003).
Matz et al., "Fluorescent proteins from nonbioluminescent Anthozoa species," Nat. Biotechnol. 17:969-973 (1999).
Patterson and Lippincott-Schwartz "A photoactivatable GFP for selective photolabeling of proteins and cells," Science. 297(5588):1873-7(2002).
Shagin et al., "GFP-like proteins as ubiquitous metazoan superfamily: evolution of functional features and structural complexity," Mol. Biol. Evol. 21(5):841-850 (2004).
Tu et al., "A naturally enhanced green fluorescent protein from magnificent sea anemone (*Heteractis magnifica*) and its functional analysis," Biochem. Biophys. Res. Commun. 301(4):879-885 (2003).
Zacharias et al., "Partitioning of lipid-modified monomeric GFPs into membrane microdomains of live cells," Science. 296(5569):913-6 (2002).
International Search Report and Written Opinion; PCT/US05/33778; mailed May 30, 2008 (10 pages).

* cited by examiner

*Primary Examiner* — Kagnew H Gebreyesus
(74) *Attorney, Agent, or Firm* — Fish & Richardson P.C.

(57) ABSTRACT

The invention includes fusion polypeptides including a first fluorescent protein, e.g., a FRET donor protein, a second fluorescent protein, e.g., a FRET acceptor protein, and, linked to at least one of the fluorescent (e.g., FRET donor or FRET acceptor) proteins, an Fc-region of an immunoglobulin. The polypeptide can be immobilized with respect to a surface via the Fc-region even in the absence of antibodies to either the FRET donor protein or FRET acceptor protein, and can be used as a calibration standard for fluorescence resonance energy transfer includes a polypeptide.

13 Claims, 6 Drawing Sheets

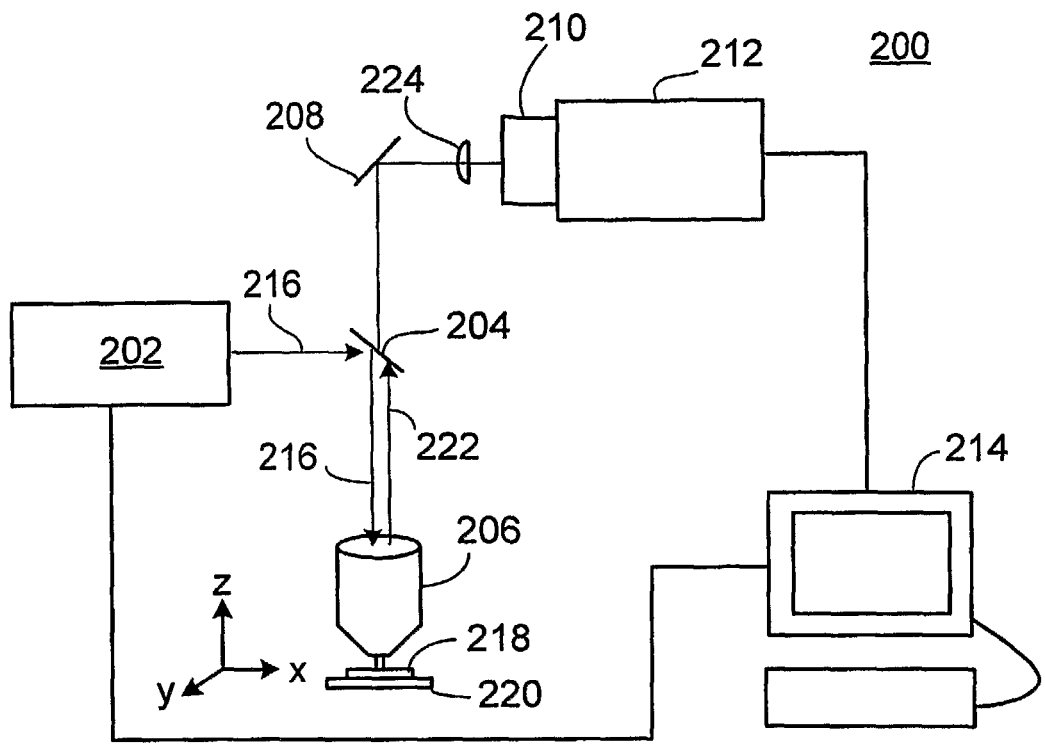
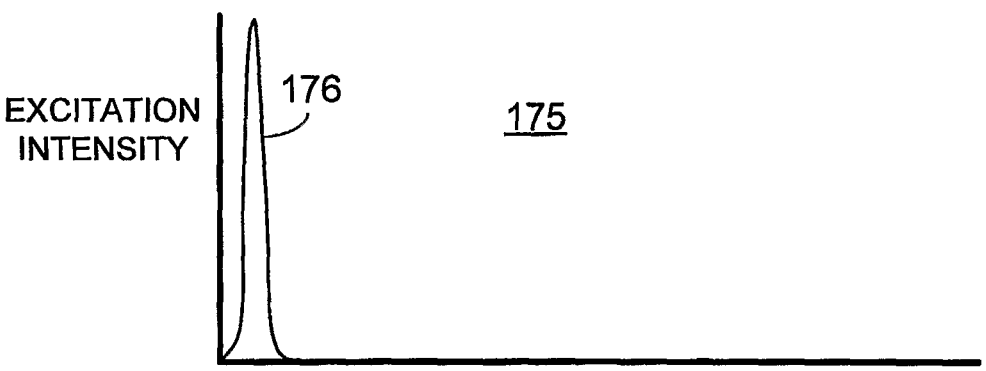
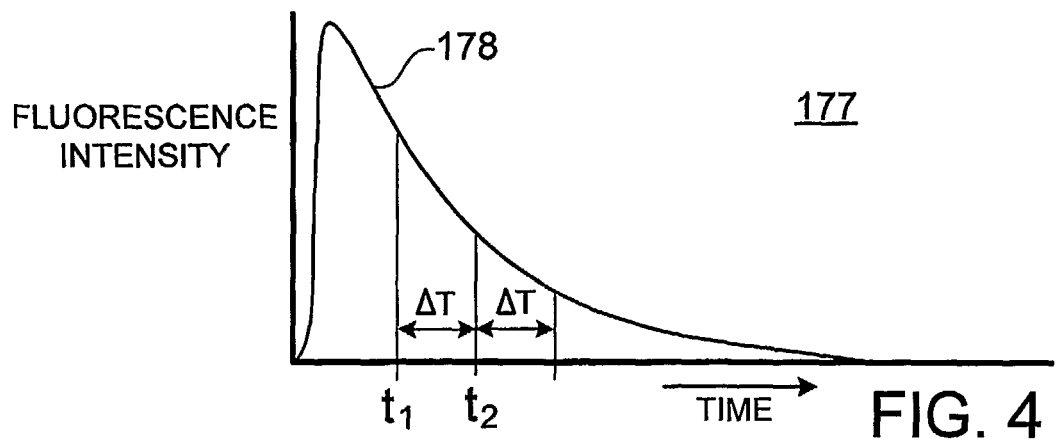
FIG. 4

FIG. 5
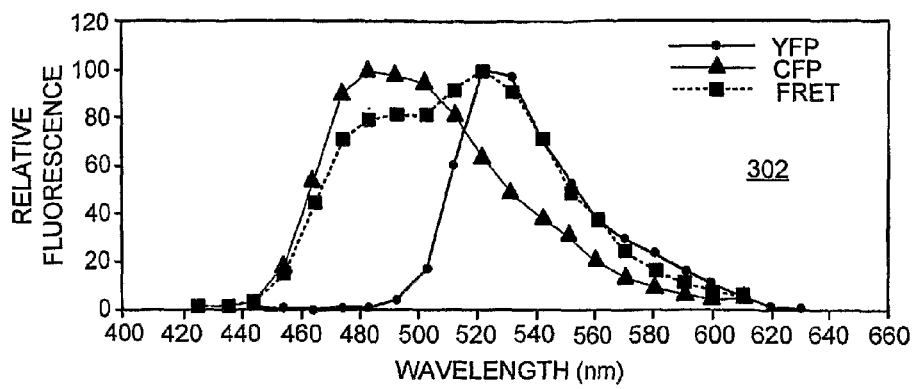
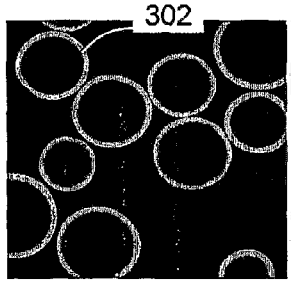
FIG. 6A
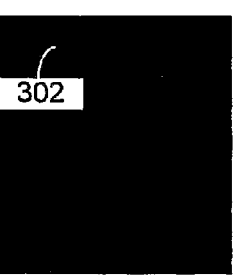
FIG. 6B
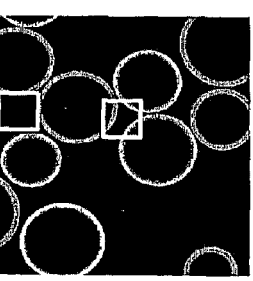
FIG. 6C
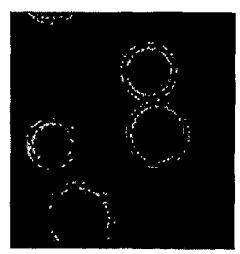
FIG. 7
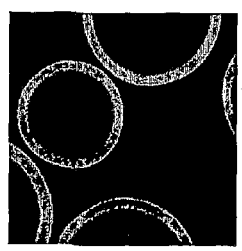
FIG. 8A
FIG. 8B
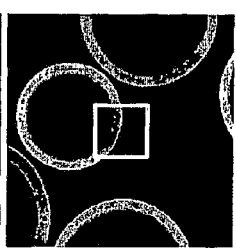
FIG. 8C
FIG. 8D

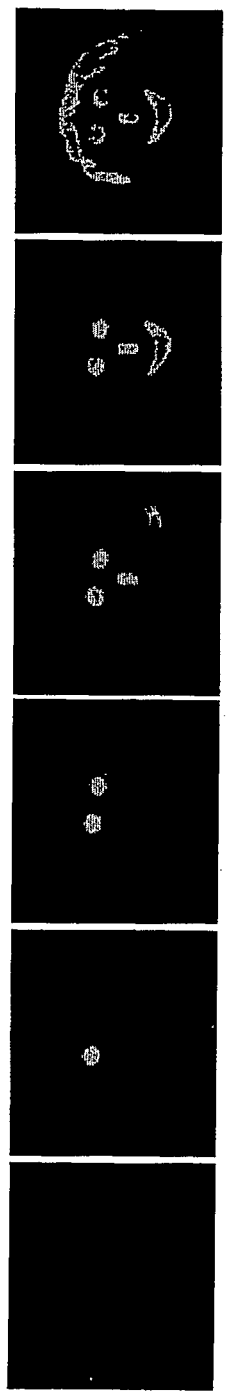

SEQUENCE LISTING

<160> NUMBER OF SEQ ID NOS: 30

<210> SEQ ID NO 1
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 1

Ile Asp Gly Arg
1

<210> SEQ ID NO 2
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 2

Asp Asp Asp Asp Lys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 3

Ala Ala Asp Asp Asp Asp Lys Ala Ala
1               5

<210> SEQ ID NO 4
<211> LENGTH: 36
<212> TYPE: DNA
<213> ORGANISM: Artificial Sequence
<220> FEATURE:
<223> OTHER INFORMATION: Primer

<400> SEQUENCE: 4
ctgaacgaat tcgccgctag catggtgagc aagggc                                 36

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
tagggcactg cggccgcctt gtacagctcg tccat                                  35

<210> SEQ ID NO 6
<211> LENGTH: 34
<212> TYPE: DNA
<213> ORGANISM: Artificial Sequence
<220> FEATURE:
<223> OTHER INFORMATION: P

<400> SEQUENCE: 6
gaccgaaaag cttatggtga gcaagggcga ggag                                   34

<210> SEQ ID NO 7
<211> LENGTH: 40
<212> TYPE: DNA
<213> ORGANISM: Artificial Sequence
<220> FEATURE:
<223> OTHER INFORMATION: Primer

<400> SEQUENCE: 7
gatgggaatt cggcatcgat tgccttgtac agctcgtcca           40

<210> SEQ ID NO 8
<211> LENGTH: 702
<212> TYPE: DNA
<213> ORGANISM: Mus musculus

<400> SEQUENCE: 8
gagcccagag ggcccacaat caagccctgt cctccatgca aatgcccagc acctaacctc     60
ttgggtggac catccgtctt catcttccct ccaaagatca aggatgtact catgatctcc    120
ctgagcccca tagtcacatg tgtggtggtg gatgtgagcg aggatgaccc agatgtccag    180
atcagctggt ttgtgaacaa cgtggaagta cacacagctc agacacaaac ccatagagag    240
gattacaaca gtactctccg ggtggtcagt gccctcccca tccagcacca ggactggatg    300
agtggcaagg agttcaaatg caaggtcaac aacaaagacc tcccagcgcc catcgagaga    360
accatctcaa acccaaagg gtcagtaaga gctccacagg tatatgtctt gcctccacca    420
gaagaagaga tgactaagaa acaggtcact ctgacctgca tggtcacaga cttcatgcct    480
gaagacattt acgtggagtg gaccaacaac gggaaaacag agctaaacta caagaacact    540
gaaccagtcc tggactctga tggttcttac ttcatgtaca gcaagctgag agtggaaaag    600
aagaactggg tggaaagaaa tagctactcc tgttcagtgg tccacgaggg tctgcacaat    660
caccacacga ctaagagctt ctcccggact ccgggtaaat ga                      702

<210> SEQ ID NO 9
<211> LENGTH: 44
<212> TYPE: DNA
<213> ORGANISM: Artificial Sequence
<220> FEATURE:
<223> OTHER INFORMATION: Primer

<400> SEQUENCE: 9
tcacctgtgc ggccgcgggg ggcgagccca gagggcccac aatc           44

<210> SEQ ID NO 10
<211> LENGTH: 37
<212> TYPE: DNA
<213> ORGANISM: Artificial Sequence
<220> FEATURE:
<223> OTHER INFORMATION: Primer

<400> SEQUENCE: 10
ggatatctgc agaactcgag gtcgactcat ttacccg           37

<210> SEQ ID NO 11
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 11

Ala Ala Ala Gly Gly
1               5

```
<210> SEQ ID NO 12
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 12

Ala Ile Asp Ala Glu Phe Ala Ala Ser
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 13

Gly Ala Ala Gly Gly
1               5

<210> SEQ ID NO 14
<211> LENGTH: 2241
<212> TYPE: DNA
<213> ORGANISM: Artificial Sequence
<220> FEATURE:
<223> OTHER INFORMATION: Synthetically generated oligonucleotide

<400> SEQUENCE: 14
atgggctgca tcaagagcaa gcgcaaggac aacctgaacg acgacggcgt ggacatgaag      60
accatggtga gcaagggcga ggagctgttc accggggtgg tgcccatcct ggtcgagctg     120
gacggcgacg taaacggcca caggttcagc gtgtccggcg agggcgaggg cgatgccacc     180
tacggcaagc tgaccctgaa gttcatctgc accaccggca agctgcccgt gccctggccc     240
accctcgtga ccaccctgac ctggggcgtg cagtgcttca gccgctaccc cgaccacatg     300
aagcagcacg acttcttcaa gtccgccatg cccgaaggct acgtccagga cgtaccatc     360 ttcttcaagg acgacggcaa ctacaagacc cgcgccgagg tgaagttcga gggcgacacc     420
ctggtgaacc gcatcgagct gaggggcatc gacttcaagg aggacggcaa catcctgggg     480
cacaagctgg agtacaacta catcagccac aacgtctata tcaccgccga caagcagaag     540
aacggcatca aggcccactt caagatccgc cacaacatcg aggacggcag cgtgcagctc     600
gccgaccact accagcagaa cacccccatc ggcgacggcc ccgtgctgct gcccgacaac     660
cactacctga gcacccagtc cgccctgagc aaagacccca acgagaagcg cgatcacatg     720
gtcctgaagg agttcgtgac cgccgccggg atcactctcg gcatggacga gctgtacaag     780
gcaatcgatg ccgaattcgc cgctagcatg gtgagcaagg gcgaggagct gttcaccggg     840
gtggtgccca tcctggtcga gctggacggc gacgtaaacg gccacaagtt cagcgtgtcc     900
ggcgagggcg agggcgatgc cacctacggc aagctgaccc tgaagttcat ctgcaccacc     960
ggcaagctgc ccgtgccctg gcccaccctc gtgaccacct tcggctacgg cctgaagtgc    1020
ttcgcccgct accccgacca catgaagcag cacgacttct tcaagtccgc catgcccgaa    1080
ggctacgtcc aggagcgtac catcttcttc aaggacgacg gcaactacaa gacccgcgcc    1140
gaggtgaagt tcgagggcga caccctggtg aaccgcatcg agctgaaggg catcgacttc    1200
aaggaggacg gcaacatcct ggggcacaag ctggagtaca actacaacag ccacaacgtc    1260
tatatcatgg ccgacaagca gaagaacggc atcaaggtga acttcaagat ccgccacaac    1320
```

```
atcgaggacg gcagcgtgca gctcgccgac cactaccagc agaacacccc catcggcgac    1380
ggccccgtgc tgctgcccga caaccactac ctgagctacc agtccgccct gagcaaagac    1440
cccaacgaga agcgcgatca catggtcctg ctggagcgcg tgaccgccgc cgggatcact    1500
ctcggcatgg acgagctgta caaggggggcc gcggggggcg agcccagagg gcccacaatc    1560
aagccctgtc ctccatgcaa atgcccagca cctaacctct tgggtggacc atccgtcttc    1620
atcttccctc caaagatcaa ggatgtactc atgatctccc tgagccccat agtcacatgt    1680
gtggtggtgg atgtgagcga ggatgaccca gatgtccaga tcagctggtt tgtgaacaac    1740
gtggaagtac acacagctca gacacaaacc catagagagg attacaacag tactctccgg    1800
gtggtcagtg ccctccccat ccagcaccag gactggatga gtggcaagga gttcaaatgc    1860
aaggtcaaca caaagacct cccagcgccc atcgagagaa ccatctcaaa acccaagggg    1920
tcagtaagag ctccacaggt atatgtcttg cctccaccag aagaagagat gactaagaaa    1980
caggtcactc tgacctgcat ggtcacagac ttcatgcctg aagacattta cgtggagtgg    2040
accaacaacg ggaaaacaga gctaaactac aagaacactg aaccagtcct ggactctgat    2100
ggttcttact tcatgtacag caagctgaga gtggaaaaga gaactgggt ggaaagaaat    2160 agctactcct gttcagtggt ccacgagggt ctgcacaatc accacacgac taagagcttc    2220
tcccggactc cgggtaaatg a                                              2241

<210> SEQ ID NO 15
<211> LENGTH: 34
<212> TYPE: DNA
<213> ORGANISM: Artificial Sequence
<220> FEATURE:
<223> OTHER INFORMATION: Synthetically generated oligonucleotide

<400> SEQUENCE: 15
aattcagcgg ccttgtcatc gtcatcagcg gcat                                34

<210> SEQ ID NO 16
<211> LENGTH: 34
<212> TYPE: DNA
<213> ORGANISM: Artificial Sequence
<220> FEATURE:
<223> OTHER INFORMATION: Synthetically generated oligonucleotide

<400> SEQUENCE: 16
aattcagcgg ccttgtcatc gtcatcagcg gcat                                34

<210> SEQ ID NO 17
<211> LENGTH: 29
<212> TYPE: DNA
<213> ORGANISM: Artificial Sequence
<220> FEATURE:
<223> OTHER INFORMATION: Synthetically generated oligonucleotide

<400> SEQUENCE: 17
cgatgccgct atcgacggtc gggccgctg                                      29

<210> SEQ ID NO 18
<211> LENGTH: 31
<212> TYPE: DNA
<213> ORGANISM: Artificial Sequence
<220> FEATURE:
<223> OTHER INFORMATION: Synthetically generated oligonucleotide

<400> SEQUENCE: 18
aattcagcgg cccgaccgtc gatagcggca t                                   31
```

<210> SEQ ID NO 19
<211> LENGTH: 2265
<212> TYPE: DNA
<213> ORGANISM: Artificial Sequence
<220> FEATURE:
<223> OTHER INFORMATION: Synthetically generated oligonucleotide

<400> SEQUENCE: 19

| | | | | | | |
|---|---|---|---|---|---|---|
| atgggctgca | tcaagagcaa | gcgcaaggac | aacctgaacg | acgacggcgt | ggacatgaag | 60 |
| accatggtga | gcaagggcga | ggagctgttc | accggggtgg | tgcccatcct | ggtcgagctg | 120 |
| gacggcgacg | taaacggcca | caggttcagc | gtgtccggcg | agggcgaggg | cgatgccacc | 180 |
| tacggcaagc | tgaccctgaa | gttcatctgc | accaccggca | agctgcccgt | gccctggccc | 240 |
| accctcgtga | ccaccctgac | ctggggcgtg | cagtgcttca | gccgctaccc | cgaccacatg | 300 |
| aagcagcacg | acttcttcaa | gtccgccatg | cccgaaggct | acgtccagga | gcgtaccatc | 360 |
| ttcttcaagg | acgacggcaa | ctacaagacc | cgcgccgagg | tgaagttcga | gggcgacacc | 420 |
| ctggtgaacc | gcatcgagct | gaagggcatc | gacttcaagg | aggacggcaa | catcctgggg | 480 |
| cacaagctgg | agtacaacta | catcagccac | aacgtctata | tcaccgccga | caagcagaag | 540 |
| aacggcatca | aggcccactt | caagatccgc | cacaacatcg | aggacggcag | cgtgcagctc | 600 |
| gccgaccact | accagcagaa | cacccccatc | ggcgacggcc | ccgtgctgct | gcccgacaac | 660 |
| cactacctga | gcacccagtc | cgccctgagc | aaagacccca | acgagaagcg | cgatcacatg | 720 |
| gtcctgaagg | agttcgtgac | cgccgccggg | atcactctcg | gcatggacga | gctgtacaag | 780 |
| gcaatcgatg | ccgctgatga | cgatgacaag | gccgctgaat | cgccgctag | catggtgagc | 840 |
| aagggcgagg | agctgttcac | cggggtggtg | cccatcctgg | tcgagctgga | cggcgacgta | 900 |
| aacggccaca | gttcagcgt | gtccggcgag | ggcgagggcg | atgccaccta | cggcaagctg | 960 |
| accctgaagt | tcatctgcac | caccggcaag | ctgcccgtgc | cctggcccac | cctcgtgacc | 1020 |
| accttcggct | acggcctgaa | gtgcttcgcc | cgctaccccg | accacatgaa | gcagcacgac | 1080 |
| ttcttcaagt | ccgccatgcc | cgaaggctac | gtccaggagc | gcaccatctt | cttcaaggac | 1140 |
| gacggcaact | acaagacccg | cgccgaggtg | aagttcgagg | gcgacaccct | ggtgaaccgc | 1200 |
| atcgagctga | agggcatcga | cttcaaggag | gacggcaaca | tcctggggca | caagctggag | 1260 |
| tacaactaca | acagccacaa | cgtctatatc | atggccgaca | agcagaagaa | cggcatcaag | 1320 |
| gtgaacttca | gatccgcca | caacatcgag | gacggcagcg | tgcagctcgc | cgaccactac | 1380 |
| cagcagaaca | cccccatcgg | cgacggcccc | gtgctgctgc | ccgacaacca | ctacctgagc | 1440 |
| taccagtccg | ccctgagcaa | agaccccaac | gagaagcgcg | atcacatggt | cctgctggag | 1500 |
| cgcgtgaccg | ccgccgggat | cactctcggc | atggacgagc | tgtacaaggg | ggccgcgggg | 1560 |
| ggcgagccca | gagggcccac | aatcaagccc | tgtcctccat | gcaaatgccc | agcacctaac | 1620 |
| ctcttgggtg | gaccatccgt | cttcatcttc | cctccaaaga | tcaaggatgt | actcatgatc | 1680 |
| tccctgagcc | ccatagtcac | atgtgtggtg | gtggatgtga | gcgaggatga | cccagatgtc | 1740 |
| cagatcagct | ggtttgtgaa | caacgtggaa | gtacacacag | ctcagacaca | aacccataga | 1800 |
| gaggattaca | acagtactct | ccgggtggtc | agtgccctcc | ccatccagca | ccaggactgg | 1860 |
| atgagtggca | aggagttcaa | atgcaaggtc | aacaacaaag | acctcccagc | gcccatcgag | 1920 |
| agaaccatct | caaacccaa | agggtcagta | agagctccac | aggtatatgt | cttgcctcca | 1980 |
| ccagaagaag | agatgactaa | gaaacaggtc | actctgacct | gcatggtcac | agacttcatg | 2040 |
| cctgaagaca | tttacgtgga | gtggaccaac | aacgggaaaa | cagagctaaa | ctacaagaac | 2100 |

```
actgaaccag tcctggactc tgatggttct tacttcatgt acagcaagct gagagtggaa    2160
aagaagaact gggtggaaag aaatagctac tcctgttcag tggtccacga gggtctgcac    2220
aatcaccaca cgactaagag cttctcccgg actccgggta aatga                    2265

<210> SEQ ID NO 20
<211> LENGTH: 2262
<212> TYPE: DNA
<213> ORGANISM: Artificial Sequence
<220> FEATURE:
<223> OTHER INFORMATION: Synthetically generated oligonucleotide

<400> SEQUENCE: 20
atgggctgca tcaagagcaa gcgcaaggac aacctgaacg acgacggcgt ggacatgaag      60
accatggtga gcaagggcga ggagctgttc accggggtgg tgcccatcct ggtcgagctg     120
gacggcgacg taaacggcca caggttcagc gtgtccggcg agggcgaggg cgatgccacc     180
tacggcaagc tgaccctgaa gttcatctgc accaccggca agctgcccgt gccctggccc     240
accctcgtga ccaccctgac ctggggcgtg cagtgcttca gccgctaccc cgaccacatg     300
aagcagcacg acttcttcaa gtccgccatg cccgaaggct acgtccagga cgtaccatc     360 ttcttcaagg acgacggcaa ctacaagacc cgcgccgagg tgaagttcga gggcgacacc     420
ctggtgaacc gcatcgagct gaagggcatc gacttcaagg aggacggcaa catcctgggg     480
cacaagctgg agtacaacta catcagccac aacgtctata tcaccgccga caagcagaag     540
aacggcatca aggcccactt caagatccgc cacaacatcg aggacggcag cgtgcagctc     600
gccgaccact accagcagaa caccccatc ggcgacggcc ccgtgctgct gcccgacaac     660
cactacctga gcacccagtc cgccctgagc aaagaccca acgagaagcg cgatcacatg     720
gtcctgaagg agttcgtgac cgccgccggg atcactctcg gcatggacga gctgtacaag     780
gcaatcgatg ccgctatcga cggtcgggcc gctgaattcg ccgctagcat ggtgagcaag     840
ggcgaggagc tgttcaccgg ggtggtgccc atcctggtcg agctggacgg cgacgtaaac     900
ggccacaagt tcagcgtgtc cggcgagggc gagggcgatg ccacctacgg caagctgacc     960
ctgaagttca tctgcaccac cggcaagctg cccgtgccct ggcccaccct cgtgaccacc    1020
ttcggctacg gcctgaagtg cttcgcccgc taccccgacc acatgaagca gcacgacttc    1080
ttcaagtccg ccatgcccga aggctacgtc caggagcgca ccatcttctt caaggacgac    1140
ggcaactaca agacccgcgc cgaggtgaag ttcgagggcg acaccctggt gaaccgcatc    1200
gagctgaagg gcatcgactt caaggaggac ggcaacatcc tggggcacaa gctggagtac    1260
aactacaaca gccacaacgt ctatatcatg gccgacaagc agaagaacgg catcaaggtg    1320
aacttcaaga tccgccacaa catcgaggac ggcagcgtgc agctcgccga ccactaccag    1380
cagaacaccc ccatcggcga cggccccgtg ctgctgcccg acaaccacta cctgagctac    1440
cagtccgccc tgagcaaaga ccccaacgag aagcgcgatc acatggtcct gctggagcgc    1500
gtgaccgccg ccgggatcac tctcggcatg gacgagctgt acaaggggc cgcgggggc    1560 gagcccagag ggcccacaat caagccctgt cctccatgca aatgcccagc acctaacctc    1620
ttgggtggac catccgtctt catcttccct ccaaagatca aggatgtact catgatctcc    1680
ctgagcccca tagtcacatg tgtggtggtg gatgtgagcg aggatgaccc agatgtccag    1740
atcagctggt ttgtgaacaa cgtggaagta cacacagctc agacacaaac ccatagagag    1800
gattacaaca gtactctccg ggtggtcagt gccctcccca tccagcacca ggactggatg    1860
agtggcaagg agttcaaatg caaggtcaac aacaaagacc tcccagcgcc catcgagaga    1920
```

-continued

```
accatctcaa aacccaaagg gtcagtaaga gctccacagg tatatgtctt gcctccacca     1980
gaagaagaga tgactaagaa acaggtcact ctgacctgca tggtcacaga cttcatgcct     2040
gaagacattt acgtggagtg gaccaacaac gggaaaacag agctaaacta caagaacact     2100
gaaccagtcc tggactctga tggttcttac ttcatgtaca gcaagctgag agtggaaaag     2160
aagaactggg tggaaagaaa tagctactcc tgttcagtgg tccacgaggg tctgcacaat     2220
caccacacga ctaagagctt ctcccggact ccgggtaaat ga                        2262
```

<210> SEQ ID NO 21
<211> LENGTH: 48
<212> TYPE: DNA
<213> ORGANISM: Artificial Sequence
<220> FEATURE:
<223> OTHER INFORMATION: Primer

<400> SEQUENCE: 21

```
gacgatgaat tcgccgctag catggcctcc tccgaggacg tcatcaag                    48
```

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22

```
caagcttcgg cggccgcggc gccggtggag tgg                                    33
```

<210> SEQ ID NO 23
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 23

```
Ala Ile Asp Ala Glu Phe Ala Ala Ser
1               5
```

<210> SEQ ID NO 24
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 24

```
Gly Ala Ala Gly Gly
1               5
```

<210> SEQ ID NO 25
<211> LENGTH: 1434
<212> TYPE: DNA
<213> ORGANISM: Artificial Sequence
<220> FEATURE:
<223> OTHER INFORMATION: Synthetically generated oligonucleotide

<400> SEQUENCE: 25

```
atggtgagca agggcgagga gctgttcacc ggggtggtgc ccatcctggt cgagctggac      60
ggcgacgtaa acggccacag gttcagcgtg tccggcgagg gcgagggcga tgccacctac     120
ggcaagctga ccctgaagtt catctgcacc accggcaagc tgcccgtgcc ctggcccacc     180
ctcgtgacca ccctgacctg gggcgtgcag tgcttcagcc gctaccccga ccacatgaag     240
```

```
cagcacgact tcttcaagtc cgccatgccc gaaggctacg tccaggagcg taccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacat cagccacaac gtctatatca ccgccgacaa gcagaagaac    480
ggcatcaagg cccacttcaa gatccgccac aacatcgagg acggcagcgt gcagctygcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaaggcg    720
gccgcggggg gcgagcccag agggcccaca atcaagccct gtcctccatg caaatgccca    780
gcacctaacc tcttgggtgg accatccgtc ttcatcttcc ctccaaagat caaggatgta    840
ctcatgatct ccctgagccc catagtcaca tgtgtggtgg tggatgtgag cgaggatgac    900
ccagatgtcc agatcagctg gtttgtgaac aacgtggaag tacacacagc tcagacacaa    960
acccatagag aggattacaa cagtactctc cgggtggtca gtgccctccc catccagcac   1020
caggactgga tgagtggcaa ggagttcaaa tgcaaggtca caacaaaga cctcccagcg   1080 cccatcgaga gaaccatctc aaaacccaaa gggtcagtaa gagctccaca ggtatatgtc   1140
ttgcctccac cagaagaaga gatgactaag aaacaggtca ctctgacctg catggtcaca   1200
gacttcatgc ctgaagacat ttacgtggag tggaccaaca cgggaaaac agagctaaac   1260 tacaagaaca ctgaaccagt cctggactct gatggttctt acttcatgta cagcaagctg   1320
agagtggaaa agaagaactg ggtggaaaga aatagctact cctgttcagt ggtccacgag   1380
ggtctgcaca atcaccacac gactaagagc ttctcccgga ctccgggtaa atga         1434

<210> SEQ ID NO 26
<211> LENGTH: 1434
<212> TYPE: DNA
<213> ORGANISM: Artificial Sequence
<220> FEATURE:
<223> OTHER INFORMATION: Synthetically generated oligonucleotide

<400> SEQUENCE: 26
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca cctgacctac cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaaggcg    720
gccgcggggg gcgagcccag agggcccaca atcaagccct gtcctccatg caaatgccca    780
gcacctaacc tcttgggtgg accatccgtc ttcatcttcc ctccaaagat caaggatgta    840
ctcatgatct ccctgagccc catagtcaca tgtgtggtgg tggatgtgag cgaggatgac    900
```

| | | |
|---|---|---|
| ccagatgtcc agatcagctg gtttgtgaac aacgtggaag tacacacagc tcagacacaa | 960 | |
| acccatagag aggattacaa cagtactctc cgggtggtca gtgccctccc catccagcac | 1020 | |
| caggactgga tgagtggcaa ggagttcaaa tgcaaggtca acaacaaaga cctcccagcg | 1080 | |
| cccatcgaga gaaccatctc aaaacccaaa gggtcagtaa gagctccaca ggtatatgtc | 1140 | |
| ttgcctccac cagaagaaga gatgactaag aaacaggtca ctctgacctg catggtcaca | 1200 | |
| gacttcatgc ctgaagacat ttacgtggag tggaccaaca acgggaaaac agagctaaac | 1260 | |
| tacaagaaca ctgaaccagt cctggactct gatggttctt acttcatgta cagcaagctg | 1320 | |
| agagtggaaa agaagaactg ggtggaaaga aatagctact cctgttcagt ggtccacgag | 1380 | |
| ggtctgcaca atcaccacac gactaagagc ttctcccgga ctccgggtaa atga | 1434 | |

<210> SEQ ID NO 27
<211> LENGTH: 1434
<212> TYPE: DNA
<213> ORGANISM: Artificial Sequence
<220> FEATURE:
<223> OTHER INFORMATION: Synthetically generated oligonucleotide

<400> SEQUENCE: 27

| | | |
|---|---|---|
| atggtgagca agggcgagga gctgttcacc ggggtggtgc ccatcctggt cgagctggac | 60 | |
| ggcgacgtaa acggccacaa gttcagcgtg tccggcgagg gcgagggcga tgccacctac | 120 | |
| ggcaagctga ccctgaagtt catctgcacc accggcaagc tgcccgtgcc ctggcccacc | 180 | |
| ctcgtgacca ccttcagcta cggcgtgcag tgcttcagcc gctaccccga ccacatgaag | 240 | |
| cagcacgact tcttcaagtc cgccatgccc gaaggctacg tccaggagcg caccatcttc | 300 | |
| ttcaaggacg acggcaacta caagacccgc gccgaggtga agttcgaggg cgacaccctg | 360 | |
| gtgaaccgca tcgagctgaa gggcatcgac ttcaaggagg acggcaacat cctggggcac | 420 | |
| aagctggagt acaactacaa cagccacaac gtctatatca tggccgacaa gcagaagaac | 480 | |
| ggcatcaagg ccaacttcaa gatccgccac aacatcgagg acggcagcgt gcagctcgcc | 540 | |
| gaccactacc agcagaacac ccccatcggc gacggccccg tgctgctgcc cgacaaccac | 600 | |
| tacctgagcc accagtccgc cctgagcaaa gaccccaacg agaagcgcga tcacatggtc | 660 | |
| ctgctggagt tcgtgaccgc cgccgggatc actctcggca tggacgagct gtacaaggcg | 720 | |
| gccgcggggg gcgagcccag agggcccaca atcaagccct gtcctccatg caaatgccca | 780 | |
| gcacctaacc tcttgggtgg accatccgtc ttcatcttcc ctccaaagat caaggatgta | 840 | |
| ctcatgatct cccctgagcc catagtcaca tgtgtggtgg tggatgtgag cgaggatgac | 900 | |
| ccagatgtcc agatcagctg gtttgtgaac aacgtggaag tacacacagc tcagacacaa | 960 | |
| acccatagag aggattacaa cagtactctc cgggtggtca gtgccctccc catccagcac | 1020 | |
| caggactgga tgagtggcaa ggagttcaaa tgcaaggtca acaacaaaga cctcccagcg | 1080 | |
| cccatcgaga gaaccatctc aaaacccaaa gggtcagtaa gagctccaca ggtatatgtc | 1140 | |
| ttgcctccac cagaagaaga gatgactaag aaacaggtca ctctgacctg catggtcaca | 1200 | |
| gacttcatgc ctgaagacat ttacgtggag tggaccaaca acgggaaaac agagctaaac | 1260 | |
| tacaagaaca ctgaaccagt cctggactct gatggttctt acttcatgta cagcaagctg | 1320 | |
| agagtggaaa agaagaactg ggtggaaaga aatagctact cctgttcagt ggtccacgag | 1380 | |
| ggtctgcaca atcaccacac gactaagagc ttctcccgga ctccgggtaa atga | 1434 | |

<210> SEQ ID NO 28
<211> LENGTH: 1434

```
<212> TYPE: DNA
<213> ORGANISM: Artificial Sequence
<220> FEATURE:
<223> OTHER INFORMATION: Synthetically generated oligonucleotide

<400> SEQUENCE: 28
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgaag tgcttcgccc gctacccgga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagct accagtccgc cctgagcaaa gaccccaacg agaagcgcga tcacatggtc     660
ctgctggagt tcgtgaccgc cgccgggatc actctcggca tggacgagct gtacaaggcg     720
gccgcggggg gcgagcccag agggcccaca atcaagccct gtcctccatg caaatgccca     780
gcacctaacc tcttgggtgg accatccgtc ttcatcttcc ctccaaagat caaggatgta     840
ctcatgatct ccctgagccc catagtcaca tgtgtggtgg tggatgtgag cgaggatgac     900
ccagatgtcc agatcagctg gtttgtgaac aacgtggaag tacacacagc tcagacacaa     960
acccatagag aggattacaa cagtactctc cgggtggtca gtgccctccc catccagcac    1020
caggactgga tgagtggcaa ggagttcaaa tgcaaggtca acaacaaaga cctcccagcg    1080
cccatcgaga gaaccatctc aaaacccaaa gggtcagtaa gagctccaca ggtatatgtc    1140
ttgcctccac cagaagaaga gatgactaag aaacaggtca ctctgacctg catggtcaca    1200
gacttcatgc ctgaagacat ttacgtggag tggaccaaca cgggaaaac agagctaaac    1260
tacaagaaca ctgaaccagt cctggactct gatggttctt acttcatgta cagcaagctg    1320
agagtggaaa agaagaactg ggtggaaaga aatagctact cctgttcagt ggtccacgag    1380
ggtctgcaca atcaccacac gactaagagc ttctcccgga ctccgggtaa atga          1434

<210> SEQ ID NO 29
<211> LENGTH: 40
<212> TYPE: DNA
<213> ORGANISM: Artificial Sequence
<220> FEATURE:
<223> OTHER INFORMATION: Primer

<400> SEQUENCE: 29
cgataagaag cttatggcct cctccgagga cgtcatcaag                            40

<210> SEQ ID NO 30
<211> LENGTH: 33
<212> TYPE: DNA
<213> ORGANISM: Artificial Sequence
<220> FEATURE:
<223> OTHER INFORMATION: Primer

<400> SEQUENCE: 30
caagcttcgg cggccgcggc gccggtggag tgg                                   33
```

FLUORESCENT PROTEINS AND RELATED METHODS AND COMPOUNDS

CLAIM OF PRIORITY

This application is a national phase application under 35 U.S.C. §371 of PCT International Application No. PCT/US2005/033778, filed Sep. 20, 2005, which claims the benefit under 35 U.S.C. §119(e) of U.S. Provisional Patent Application Ser. No. 60/611,457, filed on Sep. 20, 2004. The contents of these prior applications are incorporated by reference in their entirety.

FEDERALLY SPONSORED RESEARCH OR DEVELOPMENT

This invention was made with Government support under Grant No. U54 AI057159, P01 AI 57784-01, and ROI AI065783 awarded by the National Institutes of Health. The Government has certain rights in the invention.

TECHNICAL FIELD

The present invention relates to fluorescent proteins and related methods and compounds.

BACKGROUND

A number of fluorescent proteins have been described in recent years. For example, green fluorescent protein (GFP) is a native fluorescent molecule found in the jellyfish *Aequorea victoria*. Genetic modification of green fluorescent protein has led to variants, such as enhanced green fluorescent protein (EGFP), that exhibit modified fluorescence as compared to native green fluorescent protein. The variants are sometimes referred to as mutants of native green fluorescent protein.

In some cases, these variants exhibit fluorescence excitation efficiencies that are greater than the native green fluorescent molecule. Alternatively, or in combination, the variants may exhibit fluorescence at wavelengths greater or less than the native green fluorescent protein. For example, some variants include mutations within the coding sequence of GFP and these mutations lead to wavelength shifts of the GFP fluorescence into, e.g., the yellow and blue regions of the visible spectrum. Various pairs of these variants, e.g., enhanced yellow fluorescent protein (YFP) and enhanced cyan fluorescent protein (CFP), exhibit peaks for fluorescence excitation and fluorescence emission that are generally distinct from one another. Generally, however, some degree of spectral overlap remains.

Fluorescence resonance energy transfer (FRET) is a useful biophysical technique that requires some overlap between the fluorescence emission spectrum of a first molecule and the fluorescence excitation spectrum of another molecule. In FRET, a sample including a first fluorescent molecule (a FRET donor) and a second fluorescent molecule (a FRET acceptor) is irradiated with light. The donor and acceptor may interact with the light in several ways. First, the FRET donor may absorb light and emit fluorescence (referred to as donor fluorescence). Second, the FRET acceptor may absorb light and emit fluorescence (referred to as acceptor fluorescence). Additionally, the FRET donor can absorb light and transfer the energy gained to the FRET acceptor. The FRET acceptor generally emits light (FRET emission) at wavelengths characteristic of the acceptor fluorescence.

FRET requires that the FRET donor and FRET acceptor molecule be within close proximity, e.g., less than about 10 nanometers of one another. Thus, FRET can be used to probe for molecular interactions of two or more molecules within living cells. For example, interactions between molecules, e.g., proteins, receptors, and substrates, respectively labeled with a FRET-donor and FRET-acceptor can be probed (see, e.g., Clegg, "Fluorescence Resonance Energy Transfer," In: *Fluorescence Imaging Spectroscopy and Microscopy*, Wang and Herman, Eds., Wiley, New York, 1996, vol. 137, pp 179-251).

The fluorescence emission spectrum of CFP, for example, overlaps with the fluorescence excitation spectrum of YFP. Thus, CFP (the FRET donor) and YFP (the FRET acceptor) may exhibit FRET if positioned closely enough and upon the absorption of light by CFP.

To determine whether FRET has occurred, however, the FRET emission must be discriminated from the donor fluorescence and acceptor fluorescence. Several approaches are possible. One approach takes advantage of the fact that the wavelengths of the fluorescence spectra of the FRET donor and FRET acceptor are significantly different from one another. Additionally, the fluorescence excitation spectra of the FRET donor and FRET acceptor should also be significantly different. FRET emission is determined by detecting emission with various combinations of irradiating wavelengths and detection wavelengths. However, because some overlap exists between the excitation and emission spectra, calibration is required to determine the amount of FRET. In general, calibration includes measuring emission from a calibration sample having known regions of donor fluorescence, known regions of acceptor fluorescence, and known regions of FRET emission. The emission from the three regions can be used to calibrate an instrument for determining the amount of FRET observed from a sample, e.g., a cell.

In another approach, FRET emission is distinguished from donor fluorescence and acceptor fluorescence by measuring the lifetime of the detected emission. Typically, the transfer of energy from the FRET donor to the FRET acceptor shortens the lifetime of the donor fluorescence. However, because the donor fluorescence lifetime is also sensitive to environmental factors, calibration is generally required to determine whether FRET has occurred. Calibration generally involves determining the lifetime of donor fluorescence both in the presence and absence of a FRET acceptor. The lifetimes can be used to calibrate an instrument for determining the amount of FRET observed from a sample.

SUMMARY

One aspect of the present invention relates to fusion polypeptides including a first fluorescent protein and a second fluorescent protein and, linked to at least one of the first or second fluorescent proteins, an Fc-region of an immunoglobulin. The fluorescent proteins are spectrally different (i.e., have different excitation and/or emission spectra, typically both), and are not necessarily from the same species.

In some embodiments, the two fluorescent proteins are a "FRET pair," i.e., are capable of undergoing FRET with each other. In some embodiments, the fusion polypeptide also includes a third fluorescent protein, linked to one of the first or second fluorescent proteins. Generally, the three fluorescent proteins will be a "FRET trio," i.e., capable of undergoing three-way FRET. The fusion polypeptides have a number of uses, including as FRET calibration standards, and as detectors for the presence and/or activity of proteases, protease inhibitors, and Fc receptors.

The invention also includes nucleic acid molecules that encode these fusion polypeptides, as well as vectors including the nucleic acid molecules, and host cells that include or express them, e.g., cells that express the fusion polypeptides described herein. Further, the invention includes fluorescence resonance energy transfer (FRET) calibration standards that include a surface (e.g., a bead); and immobilized with respect to the surface, a plurality of the fusion polypeptides described herein.

A further aspect of the invention relates to methods for immobilizing a fusion polypeptide on a surface. The methods include contacting a surface with a fusion polypeptide as described herein, the surface having immobilized thereon a polypepticle (or fragment thereof) that binds to the Fc-region of the immunoglobulin.

Another aspect of the invention relates to methods of determining whether a cell expresses an Fc-receptor. The methods include contacting a cell with a fusion polypeptide described herein, irradiating the cell with optical radiation, and if the cell expresses an Fc-receptor, detecting fluorescence from the fluorescent protein of polypeptide bound to the cell. As used herein, "optical radiation" is light that falls in the part of the electromagnetic spectrum from the ultraviolet (UV, 200 nm) to the near infrared (NIR, 3000 nm), and includes all visible light (about 400-700 nm).

Another aspect of the invention relates to methods of determining whether a target compound blocks an Fc-receptor. The methods include combining (i) a cell that expresses an Fc-receptor, (ii) a target compound, and (iii) a fusion polypeptide as described herein, irradiating the cell with optical radiation, and if the target compound does not block the Fc-receptor, detecting fluorescence from the fluorescent protein of polypeptide bound to the receptor.

Another aspect of the invention relates to fluorescence resonance energy transfer (FRET) methods. The methods include obtaining a surface that has immobilized on it a fusion polypeptide described herein, and irradiating the surface with optical radiation, e.g., light. A fluorescence signal is then obtained from at least one of the first and second fluorescent proteins.

Another aspect of the invention relates to additional fluorescence resonance energy transfer (FRET) methods. The methods include irradiating a first polypeptide as described herein with optical radiation. A second polypeptide as described herein is also irradiated with optical radiation. One or both of the first or second polypeptides is typically immobilized with respect to a surface via the Fc-region of the second polypeptide. At least one fluorescence property of the first and/or second polypeptides is determined, e.g., emission spectrum or fluorescence lifetime.

Another aspect of the invention relates to a fluorescence resonance energy transfer (FRET) calibration standard. The standard can include a surface, and immobilized with respect to the surface, a plurality of polypeptides as described herein. In some embodiments, the surface is a bead.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 3 is a schematic of a fluorescence detection system.

FIG. 4 is a pair of graphs that illustrate a fluorescence excitation light pulse and a corresponding fluorescence decay curve.

FIG. 5 is a fluorescence intensity-wavelength plot of emission spectra from beads with cyan immobilized fluorescent protein, yellow fluorescent protein, and a fusion of cyan and yellow fluorescent proteins.

FIG. 6a is an image of a sample including the beads of FIG. 5 obtained by irradiating the beads with 458 nm light and detecting emission between 465 nm and 495 nm. The beads appear as green circles in the original.

FIG. 6b is an image of the sample of FIG. 6a obtained by irradiating the beads with 514 nm light and detecting emission between 525 and 630 nm. The beads appear as red circles in the original.

FIG. 6c is an overlay of FIGS. 6a and 6b. Those beads that appear only in 6a (medium gray) appear as green circles in the original; beads that appear only in 6b (darkest gray) are red in the original; and beads that appear in both 6a and 6b (lightest gray) are yellow in the original.

FIG. 7 is an image of FRET emission within the sample of FIG. 6a. The beads appear fuchsia with a green penumbra in the original.

FIG. 8a is an image of another sample including the beads of FIG. 5 obtained by irradiating the beads with 458 nm light and detecting emission between 465 nm and 495 nm after photobleaching a portion of the sample with 514 nm laser light. The beads appear as green circles in the original.

FIG. 8b is an image of the sample of FIG. 8a obtained by irradiating the beads with 514 nm light and detecting emission between 525 and 630 nm. The photobleached portion appears as gaps in the beads. The beads appear as red circles in the original.

FIG. 8c is an overlay of FIGS. 8a and 8b. The square shows the portion subjected to photobleaching. Those beads that appeared only in 8a (medium gray) appear as green circles in the original; beads that appeared only in 8b (darkest gray) are red in the original; and beads that appear in both 8a and 8b (lightest gray) are yellow in the original. Inside the box, the portion of the left-hand bead that was subjected to photobleaching appears as a green arc.

FIG. 8d is an image of FRET emission within the sample of FIG. 8a. The FRET beads appear to be fuchsia with a green penumbra in the original.

FIGS. 10a-10f are a series of fluorescence images of a bead coated with photoactivatable GFP. From 10a to 10f, different regions of interest have been sequentially photoactivated. The regions that appear light gray are green in the original.

DETAILED DESCRIPTION

One aspect of the present invention relates to a fusion polypeptide including a first fluorescent protein and, optionally, additional fluorescent proteins, e.g., for a total of two, three, or more. At least one of the fluorescent proteins is linked to an Fc-region of an immunoglobulin. The Fc-region can be used to, e.g., associate the peptide with a surface, e.g., a bead or a surface of a cell. Alternatively, or in combination, the Fc-region can be used to determine whether a cell includes a receptor able to bind with an Fc-region.

In embodiments including first and second fluorescent proteins, the proteins of the polypeptides typically exhibit fluorescence resonance energy transfer (FRET). The first and second proteins typically operate as a FRET pair, which can be used to, e.g., calibrate a fluorescence system, as FRET standards, or to detect the presence of proteases, protease inhibitors, or Fc receptors, inter alia.

Fluorescent Constructs and Calibration Standards

Described herein are fusion polypeptides that include at least one fluorescent protein linked to an Fc region of an immunoglobulin. In some embodiments, the fusion polypeptides include two, three, or more fluorescent proteins, all of which are spectrally different.

Figure 1:
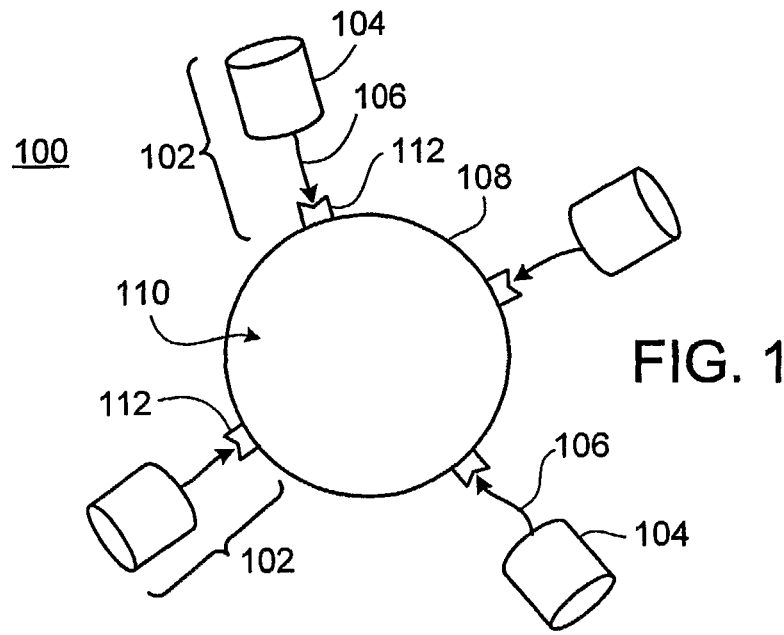
FIG. 1 is a schematic of a polypeptide 102 including a single fluorescent protein 104 and an Fc-region of an immunoglobulin 106. The polypeptide is immobilized with respect to a surface 108 of a bead 110 via the Fc-region binding to a polypeptide 112 on the surface 108.

Referring to FIG. 1, a FRET calibration standard 100 for calibrating a fluorescence detection system includes a construct 102 immobilized with respect to a surface, e.g., a surface 108 of a bead 110. Construct 102 is generally a fusion polypeptide that includes a fluorescent moiety, e.g., at least one fluorescent protein 104, and an Fc-region 106 of an immunoglobulin.

Fluorescent protein 104 emits fluorescence when excited with optical radiation. A number of such fluorescent proteins are known in the art and described herein. The emitted fluorescence typically has at least one wavelength of between about 400 nm and about 1000 nm. Fluorescent protein 104 can be, e.g., a FRET donor or a FRET acceptor. A bead 110 with a FRET donor immobilized thereto is a donor bead. A bead 110 with a FRET acceptor immobilized thereto is an acceptor bead. It should be understood that the same molecule may operate as a FRET donor in some conditions and as a FRET acceptor in other conditions.

In some embodiments, fluorescent protein 104 is a native fluorescent protein or a variant thereof, e.g., green fluorescent protein (GFP; see, e.g., Tu et al., Biochem. Biophys. Res. Commun. 301 (4), 879-885 (2003); GenBank Accession No. AAO16871), enhanced green fluorescent protein (EGFP), cyan fluorescent protein (CFP), enhanced cyan fluorescent protein (ECFP), photoactivable green fluorescent protein (paGFP) (e.g., Patterson and Lippincott-Schwartz, Science. 297(5588):1873-7 (2002)); yellow fluorescent protein (YFP), enhanced yellow fluorescent protein (EYFP), Blue Fluorescent Protein (BFP), Red Fluorescent Protein (RFP), monomeric RFP (mRFP) (Campbell et al., Proc. Natl. Acad. Sci. U.S.A. 99(12):7877-82 (2002); GenBank Accession No. AF506027.1), dimeric red fluorescent protein (GenBank Accession No. AF506025.1); tandem-dimer red fluorescent protein (GenBank Accession No. AF506026.1); JRed (Shagin et al., Mol. Biol. Evol. (2004) 21(5):841-850), Kindling Red (Chudakov et al., Nature Biotechnology (2003) February; 21(2):191-194), or an enhanced version thereof. In some embodiments, the fluorescent protein is a reef coral fluorescent protein (RCFP) or variant thereof, e.g., *Anemonia majano* cyan fluorescent protein (AmCyan), *Zoanthus* sp. green fluorescent protein (ZsGreen), *Zoanthus* sp. yellow fluorescent protein (ZsYellow), *Discosoma* sp red fluorescent protein (DsRed), *Anemonia sulcata* fluorescent protein (AsRed), and *Heteractis crispa* red fluorescent protein (HcRed). Vectors including nucleic acid sequences encoding fluorescent proteins and variants thereof are known in the art and are available from, e.g., BD Biosciences Clontech, Palo Alto, Calif.

Other fluorescent proteins include amajGFP (amFP486) (GenBank Accession No. AF168421), dstrGFP (dsFP483) (GenBank Accession No. AF168420), clavGFP (cFP484) (GenBank Accession No. AF168424), cgigGFP (GenBank Accession No. M62653), hcriGFP (GenBank Accession No. AF420592), ptilGFP (GenBank Accession No. AY015995), rmueGFP (GenBank Accession No. AY015996), zoanGFP (zFP506) (GenBank Accession No. AF168422), asulGFP (asFP499) (GenBank Accession No. AF322221), dis3GFP (GenBank Accession No. AF420593), dendGFP (GenBank Accession No. AF420591), mcavGFP (GenBank Accession No. AY037769), rfloGFP (GenBank Accession No. AY037772), scubGFP1 (GenBank Accession No. AY037767), scubGFP2 (GenBank Accession No. AY037771), zoanYFP (zFP538) (GenBank Accession No. AF168423), DsRed (drFP583) (GenBank Accession No. AF168419), dis2REP (dsFP593) (GenBank Accession No. AF272711), zoan2RFP (GenBank Accession No. AY059642), cpFP611 (GenBank Accession No. AY130757), mcavRFP (GenBank Accession No. AY037770) rfloRFP (GenBank Accession No. AY037773), Kaede (GenBank Accession No. AB085641), asulCP (asCP) (GenBank Accession No. AF246709), hciCP (hcCP) (GenBank Accession No. AF363776), cgigCP (cgCP) (GenBank Accession No. AF363775), cpasCP (cpCP) (GenBank Accession No. AF383155), gtenCP (gtCP) (GenBank Accession No. AF383156).

Variants, or enhanced versions thereof, available from Clontech (Mountain View, Calif.) include AcGFP1 (Gurskaya, N. G., et al., (2003) Biochem. J. 373(Pt. 2):403-408), and reef coral fluorescent proteins (RCFPs) AmCyan, AsRed, ZsGreen, ZsYellow, DsRed, and HcRed (Matz, et al., Nat. Biotechnol. 17:969-973 (1999)). Variants, or enhanced versions thereof, e.g., those available from Evrogen (Moscow, Russia), include PhiYFP and TurboGFP (Shagin et al., Mol. Biol. Evol. 21(5):841-850 (2004)), Kindling Red (KFP-Red) (Chudakov et al., Nat. Biotechnol. 21(2): 191-194 (2003)), JRed (Shagin et al., Mol. Biol. Evol. 21(5):841-850 (2004)), and PS-CFP2 (Chudakov et al., Nat. Biotechnol. 22(11): 1435-1439 (2004)). Variants, or enhanced versions thereof, available from Promega Corporation, Madison, Wis., include hMGFP (GenBank Accession No. AY218848). Vectors including nucleic acid sequences encoding fluorescent proteins and variants thereof are known in the art and are available from the respective companies.

The Fc-region 106 is typically derived from (i.e., based on a part of the sequence of) an immunoglobulin of a mammal, e.g., a mouse, a rat, a rabbit, guinea pig, cow, horse, pig, or a human. Exemplary isotypes include mouse IgG1 (GenBank Accession No. M6042), mouse IgG2a (GenBank Accession No. BC018365), mouse IgG2b (GenBank Accession No. U62650 and BF135247), mouse IgG3 (GenBank Accession No. MMIGG10G), rat IgG2a (GenBank Accession No. BC088254), human IgG1 (GenBank Accession No AF237583), human IgG2 (GenBank Accession No. AY372691), human IgG3 (GenBank Accession No. M97802), and human IgG4 (GenBank Accession No. AF237586). In some embodiments, the Fc-region is the region of an immunoglobulin to which one or more polypeptides can bind. Examples of such polypeptides include protein A, e.g., protein A derived from the cell wall of *Staphylococcus aureus*, protein G, e.g., protein G derived from the cell wall of β-hemolytic Streptococci, and/or protein L.

Typically, construct 102 is prepared by subcloning a nucleic acid encoding the Fc-region of an immunoglobulin, e.g., mouse IgG2a, in frame with a nucleic acid expressing a fluorescent protein, e.g., as described herein, e.g., CFP, GFP, YFP, paGFP, RFP, mRFP1, or HcRed, using methods known in the art (see, e.g., Sambrook et al., *Molecular Cloning: A Laboratory Manual*. 2nd, ed., Cold Spring Harbor Laboratory, Cold Spring Harbor Laboratory Press, Cold Spring Harbor, N.Y. (2001)). In some embodiments, the Fc-region is fused to the fluorescent protein via a short linker, e.g., a 5 amino acid linker, e.g., including glycine and/or alanine residues. The resulting nucleic acid can be inserted into a mammalian expression vector and/or into a retrovirus, which can then be used to transfect or infect cells, e.g., human embryonic kidney (HEK) cells, in order to express the protein in the cells. After transfection, the cells can be sorted, e.g., using a flow cytometer, such as a Becton Dickinson Vantage cell sorter, to identify high expressers of the construct. The high expressers can be cultured and lysed to release construct 102.

Generally, where two fluorescent proteins are included in the construct, they are separated by a linker 130. Linker 130 determines the distance separating proteins 104 and 128, e.g., between a FRET donor and FRET acceptor. The distance between the linked proteins 104 and 128 of a given construct is typically on the order of 10 nm or less. Because the distance is so small, the nearest neighbor of each protein is almost always the other protein of the same construct. Thus, the average distance between a FRET donor and nearest FRET acceptor is essentially independent of concentration. Moreover, even when small numbers of fusion polypeptides are bound to a surface, the distribution of the distances between FRET donors and nearest FRET acceptors is substantially smaller than the average distance.

The average length of, for example, a 15 amino acid linker can extend to 50 Å (5 µm). Thus in general the linker can have up to about 30 amino acids. One of skill in the art will appreciate that the length depends on the conformation and flexibility of the linker, which are determined by the amino acid composition. In general, three different kinds of linkers can be introduced, as follows:

1. Short linkers, which create most efficient FRET. The length and the rigidity of the linker can be varied to produce beads with different FRET efficiencies. One can even use rigid linkers of a length that would prevent FRET as another control (e.g., with a double positive construct that does not FRET). Having a different range of beads with different efficiencies is useful if one aims at measuring distances between molecules—this can serve as another standard.

2. Linkers containing a defined enzyme cleavage site, such as a protease cleavage site. These beads can be used for screening drug libraries for molecules that inhibit the cleavage of a certain protease (e.g., viral proteases, such as HIV protease). These beads can be used to test whether a sample, e.g., a biological fluid (e.g., from a subject such as a human or other mammal) contains a protease activity. To do this, the beads are incubated in the respective fluid and then tested for FRET activity (e.g., by FACS or in a plate reader). Some exemplary proteases, for which inhibitors would be medically useful, include 3C-like protease of SARS coronavirus (Sun et al., Protein Expr Purif. 32(2):302-8 (2003); NS3.4A protease of hepatitis C virus (Perni, Drug News Perspect. 13(2):69-77 (2000)); caspase in hypoxia-ischemia therapy (Joly et al., J. Cereb. Blood Flow Metab. 24(1): 124-31 (2004)); Tumor necrosis factor-alpha-converting enzyme in focal ischemic brain injury (Wang et al., Mol Pharmacol. 65(4):890-6 (2004)); vasopeptidase, angiotensin-converting enzyme (ACE) and neutral endopeptidase (NEP, e.g., NEP-24.11) (Xu et al., J. Card. Fail. 10(1):83-9 (2004)); tissue plasminogen activator for acute ischaemic stroke (Jenkinson, Hosp Med. 65(3):164-9 (2004)); Beta-secretase for Alzheimer's disease (Citron, Trends Pharmacol Sci. (2):92-7 (2004)); dipeptidyl peptidase IV (DPP-IV) in diabetes (Vahl and D'Alessio, Expert Opin Investig Drugs. 13(3): 177-88 (2004)); vascular chymase in atherosclerosis and vascular disease (Doggrell and Wanstall, Cardiovasc Res. 61(4):653-62 (2004)); matrix metalloproteinase in intimal hyperplasia (Rotmans et al., J Vasc Surg. 39(2):432-9 (2004)); thrombin for anticoagulation (Nutescu and Wittkowsky, Ann Pharmacother. 38(1):99-109 (2004)); and tryptase for asthma (Zhao et al., Bioorg Med Chem Lett. 14(2):309-12 (2004)).

In some embodiments, the linker includes different chemical entities other than amino acids (e.g., DNA, RNA, carbohydrates). One can then expand the screening to DNAse, RNAs, or glycosidases.

3. Linkers including domains of proteins that undergo conformational changes, for example, sensors for calcium, phosphorylation, or other physiological conditions. With the Fc linked to such a construct, one can screen outside cells and counterscreen inside cells with the same constructs, e.g., as described in Zal and Gascoigne, Curr Opin Immunol. 16(5): 674-83 (2004).

Linker 130 also limits the variation in orientation between the proteins. That is, the orientation between the proteins is generally not random, but is determined by the respective attachment locations of linker 130 to each of the proteins.

Construct 102 is generally immobilized with respect to surface 108, such as via the Fc-region 106. Surface 108 generally includes a compound, e.g., a polypeptide 112, that binds to the Fc-region 106. Polypeptide 112 can include, e.g., at least one of protein A, protein G, protein L, or other polypeptide that binds to an Fc-region. The polypeptide can be lyophilized. Typical surfaces are on beads, such as beads suitable for flow cytometry analysis, e.g., beads having a diameter of less than about 50 µm, e.g., less than about 25 µm. The surface can also be on a plate, e.g., a multi-well plate suitable for Western blot analysis. In some embodiments, the surface is or includes, e.g., latex, agarose or Sepharose™, although other materials to which polypeptides can bind are suitable.

Calibration standard 100 can be prepared by contacting lysates released from cultured cells with surface 108 including polypeptide 112 and incubating at about 4° C. with mixing. Fc-region 106 binds to polypeptide 112 of the surface.

After a sufficient incubation time, e.g., an hour, the surface is washed to remove unbound construct and other compounds. Construct 102 may be covalently crosslinked to the surface, such as by contacting the surface and immobilized construct with triethanolamine and dimethyl pimelimidate and incubating.

Figure 2:
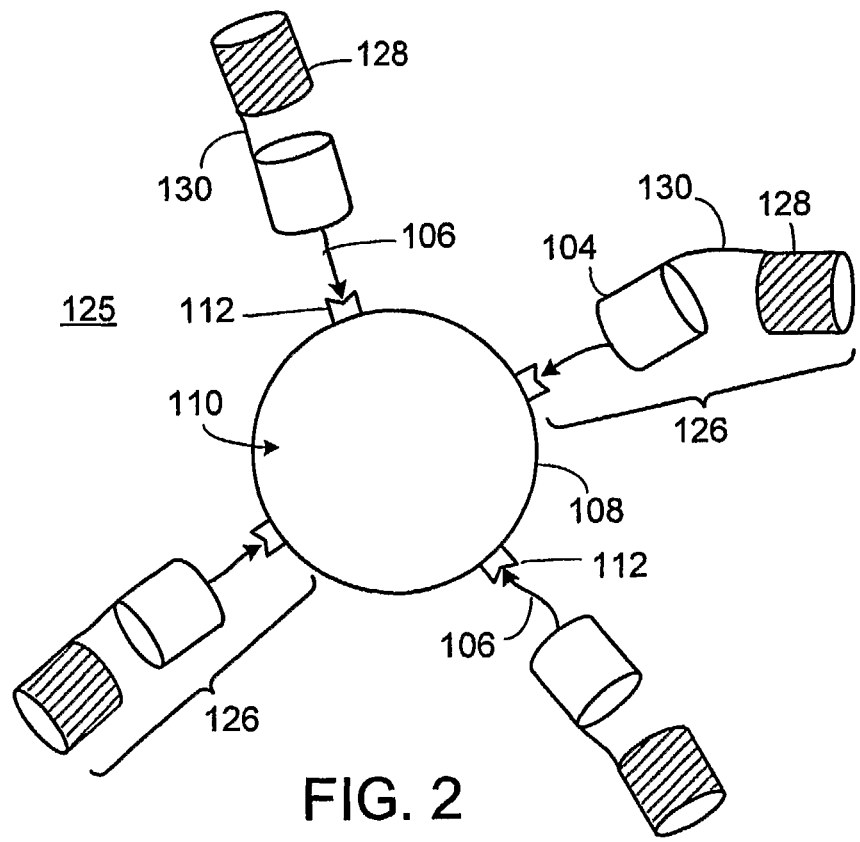
FIG. 2 is a schematic of a polypeptide 102 including two linked fluorescent proteins 104, 128, which are connected to each other by a linker 130, and an Fc-region of an immunoglobulin 106. The polypeptide is immobilized with respect to a surface 108 of a bead 110 via the Fc-region binding to a polypeptide 112 on the surface 108.

Referring to FIG. 2, a calibration standard 125 for calibrating a fluorescence detection system includes a construct 126 immobilized with respect to a surface, e.g., surface 108 of bead 110. Construct 126 is generally a polypeptide and includes at least first and second fluorescence moieties, e.g., fluorescent protein 104 and a second fluorescent protein 128 connected by a linker 130. Construct 126 also includes Fc-region 106 and may be immobilized via the Fc-region and an antigen thereto, e.g., protein A and/or protein G to surface 108.

Construct 126 can be prepared in the same manner as construct 102 except, in the final construct, the Fc-portion of an immunoglobulin is fused to a fusion of fluorescent proteins 104 and 128, e.g., linked by linker 130, such that the Fc region is at one end, in frame with the two fluorescent proteins.

Fluorescent protein 128 can include any fluorescent protein known in the art, e.g., as described herein for fluorescent protein 104, but fluorescent protein 128 is not the same (i.e., is spectrally different) as fluorescent protein 104. In some embodiments, one of proteins 104 and 128 operates as a FRET donor and the other of proteins 104, 128 operates as a FRET acceptor. Typically, the absorption and emission spectra of the proteins 104, 128 are configured such that a fluorescence emission spectrum of one of the proteins, e.g., protein 104, overlaps a fluorescence excitation spectrum of the other protein, e.g., protein 128. Additionally, proteins 104, 128 have fluorescence emission spectra that can be distinguished from one another. Accordingly, for example, protein 104 may transfer optical excitation to protein 128 via FRET. Protein 128 emits fluorescence, which may generally be distinguished from fluorescence emitted by protein 104. One of skill in the art will appreciate that either of fluorescent proteins 104 or 128 can be the FRET donor, and the other the FRET acceptor.

In some embodiments, one of proteins 104, 128 has a fluorescence excitation spectrum having a maximum of between about 300 nm and about 425 nm and the other of proteins 104, 128 has a fluorescence excitation spectrum having a maximum of between about 450 nm and about 550 nm. In other embodiments, one of proteins 104, 128 has a fluorescence excitation spectrum having a maximum of between about 375 nm and about 475 nm and the other of proteins 104, 128 has a fluorescence excitation spectrum having a maximum of between about 500 nm and about 575 nm.

Exemplary combinations include CFP-YFP, GFP-mRFP1, YFP-mRFP1, or GFP-RFP. In some embodiments, one of the fluorescent proteins is photoactivatable, e.g., paGFP. With, for example, a paGFP-RFP combination, FRET could be switched on, e.g., in a subset of molecules by photoactivating the GFP only in those molecules, and the FRET can be followed over time in that subset of molecules (i.e., the ones that were GFP-activated). This methodology can be used to study the trafficking in both time and space of a molecule pair that FRETs.

Also included herein are polypeptides that include three or more fluorescent proteins linked together and to an Fc region. Exemplary polypeptides include CFP-YFP-RFP, CFP-YFP-mRFP1, BFP-GFP-RFP, Cerulean-GFP-RFP, or Cerulean-YFP-RFP linked together. These polypeptides can be used to measure three-way FRET: one excites the CFP and can measure YFP and/or RFP emission, e.g., FRET between CFP and YFP and FRET between YFP and RFP (excited by CFP induced FRET to YFP). These triple fluorescent constructs can be used, e.g., as controls for experiments in which three or more fluorescent proteins are linked to receptors to measure FRET between different partners, to probe larger molecular complexes.

The polypeptides described herein, e.g., constructs 102 and 126 as well as calibration standards 100 and 125, have a variety of applications, a number of which are described herein. For example, a bead 110 with polynucleotide 126 including a FRET donor and FRET acceptor immobilized thereto can be used as a FRET bead.

Instrumentation for Fluorescence Detection

Referring to FIG. 3, a fluorescence detection system 200 includes a light source 202, a beam splitter 204, a focusing optic 206, a mirror 208, a wavelength selector 210, a detector 212, and a processor, e.g., a computer, 214. In some embodiments, fluorescence detection system can be an optical microscope, e.g., an Olympus BX60 upright epifluorescence microscope, an Olympus IX70 inverted epifluorescence microscope, or a Leica SP2 AOBS confocal microscope. One of skill in the art will appreciate that any fluorescent microscope with appropriate filter sets, or any confocal system, could also be used.

In general, light source 202 emits an excitation beam 216 having a wavelength and intensity sufficient to excite detectable fluorescence and FRET emission from various fluorescent proteins. The excitation beam generally includes at least one wavelength in the region of from about 350 nm to about 800 nm, although wavelengths outside this region may be used. Typically, the light source is a laser, e.g., a Ti:Sapphire laser with a frequency doubler, an argon laser, a krypton laser, a helium neon laser, or a diode laser. Alternatively, or in combination, an incoherent light source such as a quartz tungsten halogen lamp or mercury lamp can be used. Where the light source emits broadband optical radiation, the fluorescence detection system 200 includes an excitation wavelength selector configured to select a more narrow range of wavelengths from the broadband radiation.

In some embodiments the light source is a pulsed source that emits pulses having a width of less than the fluorescence lifetime of common fluorescence proteins. For example, the pulses may have a width of less than about 5 nanoseconds, less than about 500 picoseconds, or less than about 100 picoseconds. The light source can be a light source that emits light modulated at radio frequencies. Typically, the modulation is sinusoidal. Operation of the light source 202 is under the control of processor 214.

Beam splitter 204 receives excitation beam 216 and directs the beam toward the focusing optic 206. The beam splitter is typically a transmission beam splitter, e.g., a beam splitter that reflects light having a wavelength below a given value and transmits light having a wavelength above the given value. The reflected light has wavelengths suitable for exciting fluorescence from fluorophores, e.g., fluorescent proteins, and the transmitted light has wavelengths typically emitted by such fluorophores. The beam splitter may include a dichroic mirror.

In some embodiments, the beam splitter reflects light having wavelengths of less than about 500 nm, e.g., a range of about 335 to about 380 nm or a range of about 425 to about 490 nm. In some embodiments, the beam splitter transmits light having wavelengths of more than about 500 nm, e.g., a range of about 505 to about 800 mm.

Focusing optic 215 receives excitation beam 216 and focuses the beam within a sample 218. Focusing optic 206 may be a microscope objective. In some embodiments, the focusing object generally has a magnification of at least about 10× and less than about 100×. The numerical aperture (NA) of the focusing optic may be at least about 0.3, at least about 0.5, at least about 1.0, e.g., about 1.2. In some embodiments, optic 206 focuses excitation beam 216 to a diffraction limited spot, e.g., a spot having a radius of less than about 5 µm, less than about 2 µm, or less than about 1 µm perpendicular to the beam axis, although larger spot sizes may be used.

Sample 218 may be supported by, e.g., a microscope slide, a capillary, e.g., a capillary of a cell sorting system, a microtitre tray, or other structure suitable for supporting a sample for fluorescence measurements.

In any event, system 200 is configured to allow sample 218 and excitation beam 216 to be moved relative to one another. Typically, sample 218 is supported by a translation stage 220 capable of x-y-z movement.

Focusing optic 216 collects light 222 emitted by compounds present within the detection zone, e.g., fluorescence and/or FRET emission from fluorescent proteins within the detection zone. The light 222 is directed toward beam splitter 204, which transmits the light 222 along an optical path toward the detector 212. The optical path may include beam directing optics, such as mirror 208, and other focusing optics, such as lens 224.

Wavelength selector 210 selects a subset of the wavelengths of light 222 and directs the subset toward detector 212. Selector 210 generally includes a diffractive element, e.g., a diffraction grating and/or an interference filter, e.g., a holographic interference filter. In some embodiments, the wavelength content of the detected wavelengths may be varied such as by scanning the diffraction grating of the wavelength selector.

Detector 212 is generally an imaging detector, such as a charge coupled detector (CCD) or charge injection detector (CID). Such detectors include an array of detector elements, e.g., pixels. The detector generates an electronic signal indicative of the fluorescence intensity and/or fluorescence lifetime from the sample. In some embodiments, the electronic signal is a fluorescence image composed of the fluorescence intensities detected at each of a plurality of pixels, each of which detects fluorescence from a different portion of the irradiated sample.

In some embodiments, system 200 is configured to determine a fluorescence lifetime. Fluorescence systems for determining fluorescence lifetimes typically fall into one of two categories: frequency-domain systems and time-domain systems. Frequency domain systems irradiate a sample with excitation light, which is sinusoidally modulated at radio frequencies. The detector determines the phase shift and amplitude of the fluorescence emission relative to the excitation light. The lifetime is determined based upon the phase shift and amplitude. Frequency-domain systems are discussed in Lakowicz, J. R., Principals of Fluorescence Spectroscopy, (Plenum, N.Y. 1983), which is incorporated herein by reference in its entirety.

In time-domain methods, a pulsed light source and gated detector are used. A gated detector detects light only during a specified interval of time $\Delta T$. Generally, $\Delta T$ is less than 10 nanoseconds and can be less than 1 nanosecond. When combined with a pulsed light source, a gated detector can acquire an image for time $\Delta T$ beginning a specified time $t_k$ following an excitation pulse. As discussed below, a plurality of images acquired for time $\Delta T$ beginning at different intervals $t_k$ can be used to determine the lifetime of the fluorescence observed at each pixel of the image. Time-domain systems are discussed in Methods in Molecular Biology (vol. 183) Green Fluorescent Protein: Applications and Protocols, B. W. Hicks, Ed., (Humana Press, Inc., Totowa, N.J.) pgs. 89-100 ("Humana"), which is incorporated herein in its entirety.

Processing Fluorescence and FRET Images

In a typical FRET analysis, a biological sample comprising a FRET donor and a FRET acceptor is irradiated with light and emission from the sample is detected. The presence or absence of FRET is indicative of the proximity of the FRET donor and FRET acceptor. Thus, the analysis must distinguish between donor fluorescence, acceptor fluorescence, and FRET emission. Calibration standards 100 and 125 can respectively serve as negative controls (FRET donor emission only or FRET acceptor emission only) and a positive control for (FRET emission) in experiments involving the analysis of FRET. Such experiments can include flow cytometry, epifluorescence, and confocal microscopy.

Discriminating FRET Emission from Fluorescence

A fusion polypeptide as described herein, e.g., construct 102, e.g., configured as calibration standard 100, and/or construct 126, e.g., configured as calibration standard 125, can be used to calibrate a fluorescence system for FRET analysis. In some embodiments, calibration includes obtaining three fluorescence images from a sample including each of three fusion polypeptides: (1) a first fusion polypeptide including a FRET donor, but lacking a FRET acceptor, e.g., construct 102 with protein 104 being a FRET donor; (2) a second fusion polypeptide including a FRET acceptor, but lacking the FRET donor, e.g., construct 102 with protein 104 being a FRET acceptor with respect to the protein of the first polypeptide; and (3) a third fusion polypeptide including both the FRET donor of the first fusion polypeptide and the FRET acceptor of the second fusion polypeptide, e.g., construct 126.

Typically, the first, second, and third fusion polypeptides are immobilized with respect to respective surfaces, e.g., the sample can include calibration standard 100 configured as a donor bead, a calibration standard 100 configured as an acceptor bead, and calibration standard 125 configured as a FRET bead.

Turning to the images obtained from the sample, the first image is a donor image and is obtained by (a) irradiating the sample with optical radiation within the fluorescence excitation spectrum of the FRET donor and (b) detecting emitted light within the fluorescence emission spectrum of the FRET donor. The second image is an acceptor image and is obtained by (a) irradiating the sample with optical radiation within the fluorescence excitation spectrum of the FRET acceptor and (b) detecting emitted light within the fluorescence emission spectrum of the FRET acceptor. The third image is a FRET image and is obtained by (a) irradiating the sample with optical radiation within the fluorescence excitation spectrum of the FRET donor and (b) detecting emitted light within the fluorescence emission spectrum of the FRET acceptor. Typically, a background image indicative of detector noise is also acquired. The background image is subtracted from the donor, acceptor, and FRET images prior to further processing.

Because acceptor fluorescence from the FRET acceptor is inefficiently excited during acquisition of the donor image, the acceptor beads generally do not appear in the donor image. Because FRET donor fluorescence is inefficiently excited during acquisition of the acceptor image, the donor beads generally do not appear in the acceptor image. The FRET beads, however, will appear in all three images. The FRET beads appear in the donor image because the fusion polypeptide of the FRET beads includes both the FRET donor and the FRET acceptor. Thus, the FRET image includes contributions from (a) FRET donor fluorescence, (b) FRET acceptor fluorescence, and (c) FRET emission itself.

The amount of FRET emission can be determined by correcting the light intensity detected at each pixel in the FRET image to account for the contributions of FRET donor fluorescence and FRET acceptor fluorescence at that pixel. An explanation of a method for correcting the FRET image is assisted by introducing some nomenclature. The $i^{th}$ pixel of each image may be identified as $X_u^i$, where X can be a donor image pixel "D;" an acceptor image pixel "A," or a FRET image-pixel "F." The subscript u indicates whether the $i^{th}$ pixel contains fluorescence from a donor bead "d," an acceptor bead "a," or a FRET bead "f." For example, $A_a^i$ is the fluorescence intensity from the $i^{th}$ pixel of the acceptor image in which fluorescence from an acceptor bead is detected.

The corrected FRET intensity of the $i^{th}$ pixel of the FRET image $F^{c,i}$ can be determined by:

$$F^{c,i} = F^i - (F_d/D_d)D^i - (F_a/A_a) \times A^i$$

where $F^i$ is the uncorrected fluorescence intensity of the $i^{th}$ pixel of the FRET image; $(F_d/D_d)$ is the ratio of (a) the intensity of a pixel of the FRET image to (b) the intensity of the same pixel in the donor image, where the pixel contains fluorescence from a donor bead; $D^i$ is the intensity of the $i^{th}$ pixel of the donor image; $(F_a/A_a)$ is the ratio of (a) the intensity of a different pixel of the FRET image to (b) the intensity of the same pixel in the acceptor image, where the pixel contains fluorescence from an acceptor bead, and; $A^i$ is the intensity in the $i^{th}$ pixel of the acceptor image.

The amount of FRET emission can also be determined by measuring the lifetime of the emitted light detected at each pixel of the FRET image. Fluorescence lifetime measurements can discriminate FRET from fluorescence because the occurrence of FRET shortens the fluorescence lifetime of the FRET donor.

Referring to FIG. 4, an excitation intensity-time plot 175 illustrates the time dependence of a light pulse 176 emitted by a pulsed laser. A fluorescence intensity-time plot 177 illustrates the time dependence of the fluorescence intensity 178 emitted from an arbitrary location of a sample upon irradiation with light pulse 176. The time dependence of fluorescence intensity can generally be described using one or more exponential functions, each corresponding to a different fluorescence lifetime τ.

Using a gated detector, a first image is acquired over a duration ΔT beginning a delay time $t_1$ following light pulse 176. A second image is acquired over duration ΔT beginning a later delay time $t_2$ following the light pulse. Additional images may be acquired at other delay times. The lifetime of the fluorescence emitted from each region of the sample is determined from the fluorescence images. The Humana reference, supra, discusses such techniques for determining fluorescence lifetimes.

Calibrating FRET Distance Measurements

The efficiency of FRET emission depends upon the inverse $6^{th}$ power of the distance between the FRET donor and FRET acceptor. Thus, as the distance between the two molecules increases, the FRET emission intensity rapidly decreases. FRET emission can be used, e.g., to determine the relative separation distance and orientation between a FRET donor labeled protein and a FRET acceptor labeled receptor within or upon a cell. FRET efficiency, however, also depends on other environmental factors such as ionic strength of fluid surrounding the FRET donor and acceptor, the orientation of the FRET donor and acceptor, the presence of any fluorescence quenchers and the like. Thus, estimating separation distances from FRET emission requires careful calibration.

As discussed above, the linker determines the distance and relative orientation of the fluorescent proteins (e.g., 104 and 128) of the fusion polypeptide, e.g., in construct 126. Typically, the variation in the separation distance between the fluorescent proteins in a single fusion polypeptide is small compared to the average distance separating fluorescent proteins in different fusion proteins. The range of relative movement between the two proteins is also small compared to the average distance separating different fusion proteins. Thus, the fusion polypeptides (e.g., construct 126 and calibration standard 125) can provide FRET emission from a FRET donor and FRET acceptor having a precise, essentially fixed distance and relative orientation.

The fusion polypeptides described herein can be configured in various embodiments with different respective distances separating the fluorescent proteins and/or different relative orientations of the proteins. FRET emission obtained from such fusion polypeptides provides an in-situ calibration standard for the variation of FRET efficiency with distance and/or orientation in a particular sample. The calibration standards can include a marker, e.g., a fluorophore with a characteristic emission spectrum, so that beads with different fluorescent protein separation distances can be identified in a mixture by their different emission spectra (e.g., by their color). One or more such calibration standards can be added to a sample, e.g., one or more cells including proteins and receptors marked with a FRET donor and FRET acceptor. FRET emission from the calibration standards can be used to calibrate emission from within the cells.

If the fluorescent proteins (e.g., 104 and 128) in the calibration standards were not connected, as by a linker (e.g., 130), the distance between the proteins would vary. Thus, FRET emission would arise from FRET donor and FRET acceptor molecules spaced apart by different distances. Such emission would not provide a precise in-situ calibration for the variation in FRET emission efficiency with distance in a particular sample.

Binding Assays

The fusion polypeptides described herein, e.g., constructs 102 and 126, can be configured as Fc-receptor indicators. The fusion polypeptides will bind to Fc-receptors at the surface of cells in the absence blocking agents that interfere either partially or completely with a binding interaction between the Fc-receptor and Fc-region 106 of the constructs. Alternatively, the fusion polypeptides themselves can be used as Fc-receptor blockers.

A fluorescence-activated cell sorter (FACS) can be used to identify and physically separate cells binding the constructs. FACS instrumentation is described in, for example, Lodish, et al. Molecular Cell Biology (4th ed.), (W.H. Freeman and Company, New York, 2000) pp 153. In general, cells in a suspension are contacted with one or more of constructs 102 and 126, which may be configured with different fluorescent proteins. The Fc-regions of the constructs are selected to covalently bind only to the Fc-receptors of particular cells to be identified and separated. Typically, any extracellular matrix and surface-protein associations between cells is disrupted prior to analysis if animal tissue or cultured cells are used. The suspension with marked cells is combined with an ionized buffer solution known as the sheath fluid.

Cells of the sheath fluid are forced to flow rapidly and single-file through the FACS instrument where they are excited by light from a focused laser beam. Each cell scatters some light and the labeled cells generate fluorescence and/or FRET emission constructs bound to Fc-receptors. The scattering and emission are detected and processed by computer. The FACS instrument can separate cells meeting particular scattering and emission criteria. For example, an electrostatic charge can be applied to cells with fluorescence intensities exceeding a particular threshold. The cells exit the instrument in single drops. Cells within electrostatically charged drops are sorted by applying an electric field to the drops.

Enzyme Assays

The linker (e.g., 130) of the fusion polypeptides described herein, e.g., construct 126, can be configured with a site susceptible to cleavage by a target enzyme, e.g., a protease. A construct so configured will emit FRET emission in the absence of an active, target enzyme. The presence of active target enzyme disrupts the linker allowing the distance between the fluorescent protein to increase. Accordingly, FRET emission decreases and the presence of the enzyme can be determined. Such constructs can be used in high-throughput assays for enzymes with a particular activity. Alternatively, or in combination, the constructs be used in assays for inhibitors of a particular enzyme. In this case, continued FRET emission in the presence of an enzyme indicates the inhibitory effect of the inhibitor.

In some embodiments, the construct with enzyme cleavable linker includes a CFP protein and a YFP protein. The enzyme may be a protease, e.g., HIV protease, Factor Xa, which is an enzyme in the clotting cascade and cleaves after the arginine residue in its preferred cleavage site Ile-Asp-Gly-Arg (SEQ ID NO: 1), or enterokinase, also referred to as Endopeptidase, which is a specific protease that cleaves after lysine at its cleavage site Asp-Asp-Asp-Asp-Lys (SEQ ID NO:2).

The cleavage sites for specific enzymes can be engineered into the protein sequence of a linker in a polynucleotide expressing construct 126. For example, the cleavage site for Enterokinase (Asp-Asp-Asp-Asp-Lys (SEQ ID NO:2)) and the cleavage site for Factor Xa protease can be cloned into the spacer between CFP and YFP using annealed oligonucleotides encoding the protease cleavage site flanked with 2 alanines on each side (e.g., for Enterokinase, Ala-Ala-Asp-Asp-Asp-Asp-Lys-Ala-Ala (SEQ ID NO:3)).

The invention is further described in the following examples, which do not limit the scope of the invention described in the claims.

EXAMPLES

Example 1

Preparation of Fret Active Constructs Including an Fc-Region

Cloning of FRET active fusion polypeptide constructs including a polypeptide with a FRET donor protein and a FRET acceptor protein typically involves at least one cloning step using both fluorescent protein coding sequences and the Fc-region accepter vector, in this case pCDNA3-Fc. The coding sequences of the fluorescent proteins are amplified by polymerase chain reaction (PCR) from, in this case, a plasmid containing the coding sequence for YFP and a plasmid containing the coding sequence for CFP (described in Zacharias et al., Science. 296(5569):913-6 (2002)).

The YFP coding sequence was amplified using the following primers:
5'-CTGAACGAATTCGCCGCTAGCATGGT-GAGCAAGGGC-3' (SEQ ID NO:4) and
5'-TAGGGCACTGCGGCCGCCTTGTA-CAGCTCGTCCAT-3' (SEQ ID NO:5).

The PCR reaction was digested with EcoR I and Not I to provide a cut product. The cut product was gel purified.

The CFP coding sequence was amplified using the following primers:
5'-GACCGAAAAGCTTATGGTGAGCAAGGGC-GAGGAG-3' (SEQ ID NO:6) and
5'-GATGGGAATTCGGCATCGATTGCCTTG-TACAGCTCGTCCA-3' (SEQ ID NO:7).

The PCR reaction was digested with Hind III and EcoR I to provide a cut product. The cut product was gel purified.

A mouse IgG2a Fc cloning vector (pCDNA3-Fc) was constructed. The sequence of mouse IgG2a Fc is as follows:

(SEQ ID NO: 8)
GAGCCCAGAGGGCCCACAATCAAGCCCTGTCCTCCATGCAAATGCCCAGC

ACCTAACCTCTTGGGTGGACCATCCGTCTTCATCTTCCCTCCAAAGATCA

AGGATGTACTCATGATCTCCCTGAGCCCCATAGTCACATGTGTGGTGGTG

GATGTGAGCGAGGATGACCCAGATGTCCAGATCAGCTGGTTTGTGAACAA

CGTGGAAGTACACACAGCTCAGACACAAACCCATAGAGAGGATTACAACA

GTACTCTCCGGGTGGTCAGTGCCCTCCCCATCCAGCACCAGGACTGGATG

AGTGGCAAGGAGTTCAAATGCAAGGTCAACAACAAAGACCTCCCAGCGCC

CATCGAGAGAACCATCTCAAAACCCAAAGGGTCAGTAAGAGCTCCACAGG

TATATGTCTTGCCTCCACCAGAAGAAGAGATGACTAAGAAACAGGTCACT

CTGACCTGCATGGTCACAGACTTCATGCCTGAAGACATTTACGTGGAGTG

GACCAACAACGGGAAAACAGAGCTAAACTACAAGAACACTGAACCAGTCC

TGGACTCTGATGGTTCTTACTTCATGTACAGCAAGCTGAGAGTGGAAAAG

AAGAACTGGGTGGAAAGAAATAGCTACTCCTGTTCAGTGGTCCACGAGGG

TCTGCACAATCACCACACGACTAAGAGCTTCTCCCGGACTCCGGGTAAAT

GA

Mouse IgG2a Fc region was amplified by PCR from a plasmid including the coding sequence for mouse IgG2a Fc directly fused to the c-terminus of human TLR4 extracellular domain using the following primers (underlined portion is Fc coding):

(SEQ ID NO: 9)
5'-TCACCTGTGCGGCCGCGGGGGGC<u>GAGCCCAGAGGGCCCACAATC</u>-3'
and (SEQ ID NO: 10)
5'-GGATATCTGCAGAACTCGAGGTCGAC<u>TCATTTACCCG</u>-3'.

The PCR reaction product was digested with Not I and Xho I to prepare a cut product. The cut product was gel purified and ligated into Not I and Xho I cut pCDNA3 (Invitrogen) to provide the vector pCDNA3-Fc. The plasmid is based on pCDNA3. There is a 15 bp spacer in front of the Fc-portion, which encodes the following 5 amino acids: AAAGG (SEQ ID NO: 11). All constructs made in this vector were fused in-frame at the c-terminus to the Fc-region using the Not I site. Both of the cut PCR products, i.e., CFP and YFP, were ligated into pCDNA3-Fc cut with Hind III and Not I in the same reaction.

The resulting plasmid encoded for a polypeptide (CFP-YFP-Fc) including CFP and YFP (5'CFP, 3'YFP') separated by a 27 bp spacer, which encoded 9 amino acids: AIDAE-FAAS (SEQ ID NO: 12), fused in-frame at the c-terminus to the mouse IgG2a Fc region, separated by a 5 amino acid spacer consisting of GAAGG (SEQ ID NO: 13).

The sequences of the resulting fusion polypeptides were as follows:

```
CFP-YFP-Fc (Fc is underlined):
                                          (SEQ ID NO: 24)
ATGGGCTGCATCAAGAGCAAGCGCAAGGACAACCTGAACGACGACGGCGT

GGACATGAAGACCATGGTGAGCAAGGGCGAGGAGCTGTTCACCGGGGTGG

TGCCCATCCTGGTCGAGCTGGACGGCGACGTAAACGGCCACAGGTTCAGC

GTGTCCGGCGAGGGCGAGGGCGATGCCACCTACGGCAAGCTGACCCTGAA

GTTCATCTGCACCACCGGCAAGCTGCCCGTGCCCTGGCCCACCCTCGTGA

CCACCCTGACCTGGGCGTGCAGTGCTTCAGCCGCTACCCCGACCACATG

AAGCAGCACGACTTCTTCAAGTCCGCCATGCCCGAAGGCTACGTCCAGGA

GCGTACCATCTTCTTCAAGGACGACGGCAACTACAAGACCCGCGCCGAGG

TGAAGTTCGAGGGCGACACCCTGGTGAACCGCATCGAGCTGAGGGGCATC

GACTTCAAGGAGGACGGCAACATCCTGGGGCACAAGCTGGAGTACAACTA

CATCAGCCACAACGTCTATATCACCGCCGACAAGCAGAAGAACGGCATCA

AGGCCCACTTCAAGATCCGCCACAACATCGAGGACGGCAGCGTGCAGCTC

GCCGACCACTACCAGCAGAACACCCCCATCGGCGACGGCCCCGTGCTGCT

GCCCGACAACCACTACCTGAGCACCCAGTCCGCCCTGAGCAAAGACCCCA

ACGAGAAGCGCGATCACATGGTCCTGAAGGAGTTCGTGACCGCCGCCGGG

ATCACTCTCGGCATGGACGAGCTGTACAAGGCAATCGATGCCGAATTCGC

CGCTAGCATGGTGAGCAAGGGCGAGGAGCTGTTCACCGGGGTGGTGCCCA

TCCTGGTCGAGCTGGACGGCGACGTAAACGGCCACAAGTTCAGCGTGTCC

GGCGAGGGCGAGGGCGATGCCACCTACGGCAAGCTGACCCTGAAGTTCAT

CTGCACCACCGGCAAGCTGCCCGTGCCCTGGCCCACCCTCGTGACCACCT

TCGGCTACGGCCTGAAGTGCTTCGCCCGCTACCCCGACCACATGAAGCAG

CACGACTTCTTCAAGTCCGCCATGCCCGAAGGCTACGTCCAGGAGCGTAC

CATCTTCTTCAAGGACGACGGCAACTACAAGACCCGCGCCGAGGTGAAGT

TCGAGGGCGACACCCTGGTGAACCGCATCGAGCTGAAGGGCATCGACTTC

AAGGAGGACGGCAACATCCTGGGGCACAAGCTGGAGTACAACTACAACAG

CCACAACGTCTATATCATGGCCGACAAGCAGAAGAACGGCATCAAGGTGA

ACTTCAAGATCCGCCACAACATCGAGGACGGCAGCGTGCAGCTCGCCGAC

CACTACCAGCAGAACACCCCCATCGGCGACGGCCCCGTGCTGCTGCCCGA

CAACCACTACCTGAGCTACCAGTCCGCCCTGAGCAAAGACCCCAACGAGA

AGCGCGATCACATGGTCCTGCTGGAGCGCGTGACCGCCGCCGGGATCACT

CTCGGCATGGACGAGCTGTACAAGGGGCCGCGGGGGGCGAGCCCAGAGG

GCCCACAATCAAGCCCTGTCCTCCATGCAAATGCCCAGCACCTAACCTCT

TGGGTGGACCATCCGTCTTCATCTTCCCTCCAAAGATCAAGGATGTACTC

ATGATCTCCCTGAGCCCCATAGTCACATGTGTGGTGGTGGATGTGAGCGA

GGATGACCCAGATGTCCAGATCAGCTGGTTTGTGAACAACGTGGAAGTAC

ACACAGCTCAGACACAAACCCATAGAGAGGATTACAACAGTACTCTCCGG

GTGGTCAGTGCCCTCCCCATCCAGCACCAGGACTGGATGAGTGGCAAGGA

GTTCAAATGCAAGGTCAACAACAAAGACCTCCCAGCGCCCATCGAGAGAA

-continued
CCATCTCAAAACCCAAAGGGTCAGTAAGAGCTCCACAGGTATATGTCTTG

CCTCCACCAGAAGAAGAGATGACTAAGAAACAGGTCACTCTGACCTGCAT

GGTCACAGACTTCATGCCTGAAGACATTTACGTGGAGTGGACCAACAACG

GGAAAACAGAGCTAAACTACAAGAACACTGAACCAGTCCTGGACTCTGAT

GGTTCTTACTTCATGTACAGCAAGCTGAGAGTGGAAAAGAAGAACTGGGT

GGAAAGAAATAGCTACTCCTGTTCAGTGGTCCACGAGGGTCTGCACAATC

ACCACACGACTAAGAGCTTCTCCCGGACTCCGGGTAAATGA.
```

Example 1A

Preparation of a CFP-YFP-Fc Fusion Polypeptide with Enterokinase and Factor Xa Cleavage Sites

The cleavage site for Enterokinase (Asp-Asp-Asp-Asp-Lys (SEQ ID NO:2)) and the cleavage site for Factor Xa protease (Ile-Asp-Gly-Arg (SEQ ID NO: 1) were cloned into the spacer between CFP and YFP in using annealed oligonucleotides encoding the protease cleavage site flanked with two alanines on each side. The following oligonucleotides can be used to create Enterokinase and Factor Xa protease cleavage sites:

```
Enterokinase oligo#1:
                                  (SEQ ID NO: 15)
5'-CGATGCCGCTGATGACGATGACAAGGCCGCTG-3'

Enterokinase oligo#2:
                                  (SEQ ID NO: 16)
5'-AATTCAGCGGCCTTGTCATCGTCATCAGCGGCAT-3'

Factor Xa oligo#1:
                                  (SEQ ID NO: 17)
5'-CGATGCCGCTATCGACGGTCGGGCCGCTG-3'

Factor Xa oligo#2:
                                  (SEQ ID NO: 18)
5'-AATTCAGCGGCCCGACCGTCGATAGCGGCAT-3'.
```

The annealed oligonucleotides, which have both 5' Cla I and 3' EcoR I overhangs, can be cloned into the spacer using these restriction enzymes.

```
CFP-EK-YFP-Fc: (includes an enterokinase protease
cleavage site, shown in bold lower case; Fc is
underlined)
                                  (SEQ ID NO: 19)
ATGGGCTGCATCAAGAGCAAGCGCAAGGACAACCTGAACGACGACGGCGT

GGACATGAAGACCATGGTGAGCAAGGGCGAGGAGCTGTTCACCGGGGTGG

TGCCCATCCTGGTCGAGCTGGACGGCGACGTAAACGGCCACAGGTTCAGC

GTGTCCGGCGAGGGCGAGGGCGATGCCACCTACGGCAAGCTGACCCTGAA

GTTCATCTGCACCACCGGCAAGCTGCCCGTGCCCTGGCCCACCCTCGTGA

CCACCCTGACCTGGGCGTGCAGTGCTTCAGCCGCTACCCCGACCACATG

AAGCAGCACGACTTCTTCAAGTCCGCCATGCCCGAAGGCTACGTCCAGGA

GCGTACCATCTTCTTCAAGGACGACGGCAACTACAAGACCCGCGCCGAGG

TGAAGTTCGAGGGCGACACCCTGGTGAACCGCATCGAGCTGAGGGGCATC

GACTTCAAGGAGGACGGCAACATCCTGGGGCACAAGCTGGAGTACAACTA
```

-continued

CATCAGCCACAACGTCTATATCACCGCCGACAAGCAGAAGAACGGCATCA
AGGCCCACTTCAAGATCCGCCACAACATCGAGGACGGCAGCGTGCAGCTC
GCCGACCACTACCAGCAGAACACCCCCATCGGCGACGGCCCCGTGCTGCT
GCCCGACAACCACTACCTGAGCACCCAGTCCGCCCTGAGCAAAGACCCCA
ACGAGAAGCGCGATCACATGGTCCTGAAGGAGTTCGTGACCGCCGCCGGG
ATCACTCTCGGCATGGACGAGCTGTACAAGGCAATCGATGCCgctgatga
cgatgacaaggccgctGAATTCGCCGCTAGCATGGTGAGCAAGGGCGAGG
AGCTGTTCACCGGGGTGGTGCCCATCCTGGTCGAGCTGGACGGCGACGTA
AACGGCCACAAGTTCAGCGTGTCCGGCGAGGGCGAGGGCGATGCCACCTA
CGGCAAGCTGACCCTGAAGTTCATCTGCACCACCGGCAAGCTGCCCGTGC
CCTGGCCCACCCTCGTGACCACCTTCGGCTACGGCCTGAAGTGCTTCGCC
CGCTACCCCGACCACATGAAGCAGCACGACTTCTTCAAGTCCGCCATGCC
CGAAGGCTACGTCCAGGAGCGCACCATCTTCTTCAAGGACGACGGCAACT
ACAAGACCCGCGCCGAGGTGAAGTTCGAGGGCGACACCCTGGTGAACCGC
ATCGAGCTGAAGGGCATCGACTTCAAGGAGGACGGCAACATCCTGGGGCA
CAAGCTGGAGTACAACTACAACAGCCACAACGTCTATATCATGGCCGACA
AGCAGAAGAACGGCATCAAGGTGAACTTCAAGATCCGCCACAACATCGAG
GACGGCAGCGTGCAGCTCGCCGACCACTACCAGCAGAACACCCCCATCGG
CGACGGCCCCGTGCTGCTGCCCGACAACCACTACCTGAGCTACCAGTCCG
CCCTGAGCAAAGACCCCAACGAGAAGCGCGATCACATGGTCCTGCTGGAG
CGCGTGACCGCCGCCGGGATCACTCTCGGCATGGACGAGCTGTACAAGGG
GGCCGCGGGGGC<u>GAGCCCAGAGGGCCCACAATCAAGCCCTGTCCTCCAT</u>
<u>GCAAATGCCCAGCACCTAACCTCTTGGGTGGACCATCCGTCTTCATCTTC</u>
<u>CCTCCAAAGATCAAGGATGTACTCATGATCTCCCTGAGCCCCATAGTCAC</u>
<u>ATGTGTGGTGGTGGATGTGAGCGAGGATGACCCAGATGTCCAGATCAGCT</u>
<u>GGTTTGTGAACAACGTGGAAGTACACACAGCTCAGACACAAACCCATAGA</u>
<u>GAGGATTACAACAGTACTCTCCGGGTGGTCAGTGCCCTCCCCATCCAGCA</u>
<u>CCAGGACTGGATGAGTGGCAAGGAGTTCAAATGCAAGGTCAACAACAAAG</u>
<u>ACCTCCCAGCGCCCATCGAGAGAACCATCTCAAAACCCAAAGGGTCAGTA</u>
<u>AGAGCTCCACAGGTATATGTCTTGCCTCCACCAGAAGAAGAGATGACTAA</u>
<u>GAAACAGGTCACTCTGACCTGCATGGTCACAGACTTCATGCCTGAAGACA</u>
<u>TTTACGTGGAGTGGACCAACAACGGGAAAACAGAGCTAAACTACAAGAAC</u>
<u>ACTGAACCAGTCCTGGACTCTGATGGTTCTTACTTCATGTACAGCAAGCT</u>
<u>GAGAGTGGAAAAGAAGAACTGGGTGGAAAGAAATAGCTACTCCTGTTCAG</u>
<u>TGGTCCACGAGGGTCTGCACAATCACCACACGACTAAGAGCTTCTCCCGG</u>
<u>ACTCCGGGTAAATGA</u>.

CFP-Xa-YFP-Fc: (includes a Factor Xa protease
cleavage site, shown in bold lower case; Fc is
underlined)

(SEQ ID NO: 20)
ATGGGCTGCATCAAGAGCAAGCGCAAGGACAACCTGAACGACGACGGCGT
GGACATGAAGACCATGGTGAGCAAGGGCGAGGAGCTGTTCACCGGGGTGG
TGCCCATCCTGGTCGAGCTGGACGGCGACGTAAACGGCCACAGGTTCAGC

GTGTCCGGCGAGGGCGAGGGCGATGCCACCTACGGCAAGCTGACCCTGAA
GTTCATCTGCACCACCGGCAAGCTGCCCGTGCCCTGGCCCACCCTCGTGA
CCACCCTGACCTGGGGCGTGCAGTGCTTCAGCCGCTACCCCGACCACATG
AAGCAGCACGACTTCTTCAAGTCCGCCATGCCCGAAGGCTACGTCCAGGA
GCGTACCATCTTCTTCAAGGACGACGGCAACTACAAGACCCGCGCCGAGG
TGAAGTTCGAGGGCGACACCCTGGTGAACCGCATCGAGCTGAGGGGCATC
GACTTCAAGGAGGACGGCAACATCCTGGGGCACAAGCTGGAGTACAACTA
CATCAGCCACAACGTCTATATCACCGCCGACAAGCAGAAGAACGGCATCA
AGGCCCACTTCAAGATCCGCCACAACATCGAGGACGGCAGCGTGCAGCTC
GCCGACCACTACCAGCAGAACACCCCCATCGGCGACGGCCCCGTGCTGCT
GCCCGACAACCACTACCTGAGCACCCAGTCCGCCCTGAGCAAAGACCCCA
ACGAGAAGCGCGATCACATGGTCCTGAAGGAGTTCGTGACCGCCGCCGGG
ATCACTCTCGGCATGGACGAGCTGTACAAGGCAATCGATGCCgctatcga
cggtcgggccgctGAATTCGCCGCTAGCATGGTGAGCAAGGGCGAGGAGC
TGTTCACCGGGGTGGTGCCCATCCTGGTCGAGCTGGACGGCGACGTAAAC
GGCCACAAGTTCAGCGTGTCCGGCGAGGGCGAGGGCGATGCCACCTACGG
CAAGCTGACCCTGAAGTTCATCTGCACCACCGGCAAGCTGCCCGTGCCCT
GGCCCACCCTCGTGACCACCTTCGGCTACGGCCTGAAGTGCTTCGCCCGC
TACCCCGACCACATGAAGCAGCACGACTTCTTCAAGTCCGCCATGCCCGA
AGGCTACGTCCAGGAGCGCACCATCTTCTTCAAGGACGACGGCAACTACA
AGACCCGCGCCGAGGTGAAGTTCGAGGGCGACACCCTGGTGAACCGCATC
GAGCTGAAGGGCATCGACTTCAAGGAGGACGGCAACATCCTGGGGCACAA
GCTGGAGTACAACTACAACAGCCACAACGTCTATATCATGGCCGACAAGC
AGAAGAACGGCATCAAGGTGAACTTCAAGATCCGCCACAACATCGAGGAC
GGCAGCGTGCAGCTCGCCGACCACTACCAGCAGAACACCCCCATCGGCGA
CGGCCCCGTGCTGCTGCCCGACAACCACTACCTGAGCTACCAGTCCGCCC
TGAGCAAAGACCCCAACGAGAAGCGCGATCACATGGTCCTGCTGGAGCGC
GTGACCGCCGCCGGGATCACTCTCGGCATGGACGAGCTGTACAAGGGGGC
CGCGGGGGC<u>GAGCCCAGAGGGCCCACAATCAAGCCCTGTCCTCCATGCA</u>
<u>AATGCCCAGCACCTAACCTCTTGGGTGGACCATCCGTCTTCATCTTCCCT</u>
<u>CCAAAGATCAAGGATGTACTCATGATCTCCCTGAGCCCCATAGTCACATG</u>
<u>TGTGGTGGTGGATGTGAGCGAGGATGACCCAGATGTCCAGATCAGCTGGT</u>
<u>TTGTGAACAACGTGGAAGTACACACAGCTCAGACACAAACCCATAGAGAG</u>
<u>GATTACAACAGTACTCTCCGGGTGGTCAGTGCCCTCCCCATCCAGCACCA</u>
<u>GGACTGGATGAGTGGCAAGGAGTTCAAATGCAAGGTCAACAACAAAGACC</u>
<u>TCCCAGCGCCCATCGAGAGAACCATCTCAAAACCCAAAGGGTCAGTAAGA</u>
<u>GCTCCACAGGTATATGTCTTGCCTCCACCAGAAGAAGAGATGACTAAGAA</u>
<u>ACAGGTCACTCTGACCTGCATGGTCACAGACTTCATGCCTGAAGACATTT</u>
<u>ACGTGGAGTGGACCAACAACGGGAAAACAGAGCTAAACTACAAGAACACT</u>
<u>GAACCAGTCCTGGACTCTGATGGTTCTTACTTCATGTACAGCAAGCTGAG</u>

-continued

AGTGGAAAAGAAGAACTGGGTGGAAAGAAATAGCTACTCCTGTTCAGTGG

TCCACGAGGGTCTGCACAATCACCACACGACTAAGAGCTTCTCCCGGACT

CCGGGTAAATGA.

Example 1B

Preparation of a Constitutive Fret Construct Containing YFP and mRFP Including an Fc-Region The coding sequences of the color proteins are amplified by polymerase chain reaction (PCR) from, in this case, a plasmid containing the coding sequence for YFP and a plasmid containing the coding sequence for mRFP. The YFP coding sequence was amplified using the following primers:

```
                                         (SEQ ID NO: 6)
5'-GACCGAAAAGCTTATGGTGAGCAAGGGCGAGGAG-3'
and (SEQ ID NO: 7)
5'-GATGGGAATTCGGCATCGATTGCCTTGTACAGCTCGTCCA-3.
```

The PCR reaction was digested with Hind III and EcoR I to provide a cut product. The cut product was gel purified.
The mRFP coding sequence was amplified using the following primers:

5'-GACGATGAATTCGCCGCTAGCATGGCCTCCTCCGAGGACGTCATCAAG-3' (SEQ ID NO: 21)
and

5'-CAAGCTTCGGCGGCCGCGGCGCCGGTGGAGTGG-3'. (SEQ ID NO: 22)

The PCR reaction was digested with EcoR I and Not I to provide a cut product. The cut product was gel purified. Both of the cut PCR products, i.e. YFP and MRFP were ligated into pCDNA3-Fc cut with Hind III and Not I in the same reaction. The resulting plasmid encoded for a polypeptide (YFP-mRFP-Fc) including YFP and mRFP (5'YFP, 3' mRFP') separated by a 27 nucleotide spacer, which encoded 9 amino acids: AIDAEFAAS (SEQ ID NO:23), fused in-frame at the c-terminus to the mouse IgG2a Fc region, separated by a 5 amino acid spacer consisting of GAAGG (SEQ ID NO:24).

Example 2

Preparation of Single Color Fluorescent Protein Containing Constructs Including an Fc-Region Four constructs were prepared: (1) a polypeptide including CFP linked to an Fc-region (CFP-Fc); (2) a polypeptide including EGFP linked to an Fc-region (EGFP-Fc); (3) a polypeptide including photoactivatable GFP (paGFP) linked to an Fc-region (paGFP-Fc); and (4) a polypeptide including YFP linked to an Fc-region (YFP-Fc).
Coding sequences for the respective fluorescent proteins of each of the four constructs were PCR amplified using the following primers:

```
                                         (SEQ ID NO: 6)
5'-GACCGAAAAGCTTATGGTGAGCAAGGGCGAGGAG-3'
and (SEQ ID NO: 5)
5'-TAGGGCACTGCGGCCGCCTTGTACAGCTCGTCCAT-3'.
```

Products of the PCR reactions were digested with Hind III and Not I to provide cut products. The cut products were gel purified and ligated into the Hind III and Not I cut pCDNA3-Fc plasmid prepared in Example 1. The resulting 4 plasmids expressed polypeptides with the respective green fluorescence protein variant fused in-frame at the c-terminus to the mouse IgG2a Fc region, separated by a 5 amino acid spacer consisting of AAAGG (SEQ ID NO: 11).

The sequences of the resulting fusion polypeptides were as follows (the Fc is underlined):

CFP-Fc:
(SEQ ID NO: 25)
ATGGTGAGCAAGGGCGAGGAGCTGTTCACCGGGGTGGTGCCCATCCTGGT

CGAGCTGGACGGCGACGTAAACGGCCACAGGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGACCTG

GGGCGTGCAGTGCTTCAGCCGCTACCCCGACCACATGAAGCAGCACGACT

TCTTCAAGTCCGCCATGCCCGAAGGCTACGTCCAGGAGCGTACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACATCAGCCACAAC

GTCTATATCACCGCCGACAAGCAGAAGAACGGCATCAAGGCCCACTTCAA

GATCCGCCACAACATCGAGGACGGCAGCGTGCAGCTYGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAGGCGGCCGCGGGGGGC<u>GAGCCCAGAGGGCCCACA</u>

<u>ATCAAGCCCTGTCCTCCATGCAAATGCCCAGCACCTAACCTCTTGGGTGG</u>

<u>ACCATCCGTCTTCATCTTCCCTCCAAAGATCAAGGATGTACTCATGATCT</u>

<u>CCCTGAGCCCCATAGTCACATGTGTGGTGGTGGATGTGAGCGAGGATGAC</u>

<u>CCAGATGTCCAGATCAGCTGGTTTGTGAACAACGTGGAAGTACACACAGC</u>

<u>TCAGACACAAACCCATAGAGAGGATTACAACAGTACTCTCCGGGTGGTCA</u>

<u>GTGCCCTCCCCATCCAGCACCAGGACTGGATGAGTGGCAAGGAGTTCAAA</u>

<u>TGCAAGGTCAACAACAAAGACCTCCCAGCGCCCATCGAGAGAACCATCTC</u>

<u>AAAACCCAAAGGGTCAGTAAGAGCTCCACAGGTATATGTCTTGCCTCCAC</u>

<u>CAGAAGAAGAGATGACTAAGAAACAGGTCACTCTGACCTGCATGGTCACA</u>

<u>GACTTCATGCCTGAAGACATTTACGTGGAGTGGACCAACAACGGGAAAAC</u>

<u>AGAGCTAAACTACAAGAACACTGAACCAGTCCTGGACTCTGATGGTTCTT</u>

<u>ACTTCATGTACAGCAAGCTGAGAGTGGAAAAGAAGAACTGGGTGGAAAGA</u>

-continued

AATAGCTACTCCTGTTCAGTGGTCCACGAGGGTCTGCACAATCACCACAC
GACTAAGAGCTTCTCCCGGACTCCGGGTAAATGA.

GFP-Fc:
(SEQ ID NO: 26)
ATGGTGAGCAAGGGCGAGGAGCTGTTCACCGGGGTGGTGCCCATCCTGGT
CGAGCTGGACGGCGACGTAAACGGCCACAAGTTCAGCGTGTCCGGCGAGG
GCGAGGGCGATGCCACCTACGGCAAGCTGACCCTGAAGTTCATCTGCACC
ACCGGCAAGCTGCCCGTGCCCTGGCCCACCCTCGTGACCACCCTGACCTA
CGGCGTGCAGTGCTTCAGCCGCTACCCCGACCACATGAAGCAGCACGACT
TCTTCAAGTCCGCCATGCCCGAAGGCTACGTCCAGGAGCGCACCATCTTC
TTCAAGGACGACGGCAACTACAAGACCCGCGCCGAGGTGAAGTTCGAGGG
CGACACCCTGGTGAACCGCATCGAGCTGAAGGGCATCGACTTCAAGGAGG
ACGGCAACATCCTGGGGCACAAGCTGGAGTACAACTACAACAGCCACAAC
GTCTATATCATGGCCGACAAGCAGAAGAACGGCATCAAGGTGAACTTCAA
GATCCGCCACAACATCGAGGACGGCAGCGTGCAGCTCGCCGACCACTACC
AGCAGAACACCCCCATCGGCGACGGCCCCGTGCTGCTGCCCGACAACCAC
TACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCA
TGGACGAGCTGTACAAGGCGGCCGCGGGGGGCGAGCCCAGAGGGCCCACA
ATCAAGCCCTGTCCTCCATGCAAATGCCCAGCACCTAACCTCTTGGGTGG
ACCATCCGTCTTCATCTTCCCTCCAAAGATCAAGGATGTACTCATGATCT
CCCTGAGCCCCATAGTCACATGTGTGGTGGTGGATGTGAGCGAGGATGAC
CCAGATGTCCAGATCAGCTGGTTTGTGAACAACGTGGAAGTACACACAGC
TCAGACACAAACCCATAGAGAGGATTACAACAGTACTCTCCGGGTGGTCA
GTGCCCTCCCCATCCAGCACCAGGACTGGATGAGTGGCAAGGAGTTCAAA
TGCAAGGTCAACAACAAAGACCTCCCAGCGCCCATCGAGAGAACCATCTC
AAAACCCAAAGGGTCAGTAAGAGCTCCACAGGTATATGTCTTGCCTCCAC
CAGAAGAAGAGATGACTAAGAAACAGGTCACTCTGACCTGCATGGTCACA
GACTTCATGCCTGAAGACATTTACGTGGAGTGGACCAACAACGGGAAAAC
AGAGCTAAACTACAAGAACACTGAACCAGTCCTGGACTCTGATGGTTCTT
ACTTCATGTACAGCAAGCTGAGAGTGGAAAAGAAGAACTGGGTGGAAAGA
AATAGCTACTCCTGTTCAGTGGTCCACGAGGGTCTGCACAATCACCACAC
GACTAAGAGCTTCTCCCGGACTCCGGGTAAATGA.

PaGFP-Fc:
(SEQ ID NO: 27)
ATGGTGAGCAAGGGCGAGGAGCTGTTCACCGGGGTGGTGCCCATCCTGGT
CGAGCTGGACGGCGACGTAAACGGCCACAAGTTCAGCGTGTCCGGCGAGG
GCGAGGGCGATGCCACCTACGGCAAGCTGACCCTGAAGTTCATCTGCACC
ACCGGCAAGCTGCCCGTGCCCTGGCCCACCCTCGTGACCACCTTCAGCTA
CGGCGTGCAGTGCTTCAGCCGCTACCCCGACCACATGAAGCAGCACGACT
TCTTCAAGTCCGCCATGCCCGAAGGCTACGTCCAGGAGCGCACCATCTTC
TTCAAGGACGACGGCAACTACAAGACCCGCGCCGAGGTGAAGTTCGAGGG
CGACACCCTGGTGAACCGCATCGAGCTGAAGGGCATCGACTTCAAGGAGG

-continued

ACGGCAACATCCTGGGGCACAAGCTGGAGTACAACTACAACAGCCACAAC
GTCTATATCATGGCCGACAAGCAGAAGAACGGCATCAAGGCCAACTTCAA
GATCCGCCACAACATCGAGGACGGCAGCGTGCAGCTCGCCGACCACTACC
AGCAGAACACCCCCATCGGCGACGGCCCCGTGCTGCTGCCCGACAACCAC
TACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCA
TGGACGAGCTGTACAAGGCGGCCGCGGGGGgCGAGCCCAGAGGGCCCACA
ATCAAGCCCTGTCCTCCATGCAAATGCCCAGCACCTAACCTCTTGGGTGG
ACCATCCGTCTTCATCTTCCCTCCAAAGATCAAGGATGTACTCATGATCT
CCCTGAGCCCCATAGTCACATGTGTGGTGGTGGATGTGAGCGAGGATGAC
CCAGATGTCCAGATCAGCTGGTTTGTGAACAACGTGGAAGTACACACAGC
TCAGACACAAACCCATAGAGAGGATTACAACAGTACTCTCCGGGTGGTCA
GTGCCCTCCCCATCCAGCACCAGGACTGGATGAGTGGCAAGGAGTTCAAA
TGCAAGGTCAACAACAAAGACCTCCCAGCGCCCATCGAGAGAACCATCTC
AAAACCCAAAGGGTCAGTAAGAGCTCCACAGGTATATGTCTTGCCTCCAC
CAGAAGAAGAGATGACTAAGAAACAGGTCACTCTGACCTGCATGGTCACA
GACTTCATGCCTGAAGACATTTACGTGGAGTGGACCAACAACGGGAAAAC
AGAGCTAAACTACAAGAACACTGAACCAGTCCTGGACTCTGATGGTTCTT
ACTTCATGTACAGCAAGCTGAGAGTGGAAAAGAAGAACTGGGTGGAAAGA
AATAGCTACTCCTGTTCAGTGGTCCACGAGGGTCTGCACAATCACCACAC
GACTAAGAGCTTCTCCCGGACTCCGGGTAAATGA.

YFP-Fc:
(SEQ ID NO: 28)
ATGGTGAGCAAGGGCGAGGAGCTGTTCACCGGGGTGGTGCCCATCCTGGT
CGAGCTGGACGGCGACGTAAACGGCCACAAGTTCAGCGTGTCCGGCGAGG
GCGAGGGCGATGCCACCTACGGCAAGCTGACCCTGAAGTTCATCTGCACC
ACCGGCAAGCTGCCCGTGCCCTGGCCCACCCTCGTGACCACCTTCGGCTA
CGGCCTGAAGTGCTTCGCCCGCTACCCCGACCACATGAAGCAGCACGACT
TCTTCAAGTCCGCCATGCCCGAAGGCTACGTCCAGGAGCGCACCATCTTC
TTCAAGGACGACGGCAACTACAAGACCCGCGCCGAGGTGAAGTTCGAGGG
CGACACCCTGGTGAACCGCATCGAGCTGAAGGGCATCGACTTCAAGGAGG
ACGGCAACATCCTGGGGCACAAGCTGGAGTACAACTACAACAGCCACAAC
GTCTATATCATGGCCGACAAGCAGAAGAACGGCATCAAGGTGAACTTCAA
GATCCGCCACAACATCGAGGACGGCAGCGTGCAGCTCGCCGACCACTACC
AGCAGAACACCCCCATCGGCGACGGCCCCGTGCTGCTGCCCGACAACCAC
TACCTGAGCTACCAGTCCGCCCTGAGCAAAGACCCCAACGAGAAGCGCGA
TCACATGGTCCTGCTGGAGTTCGTGACCGCCGCCGGGATCACTCTCGGCA
TGGACGAGCTGTACAAGGCGGCCGCGGGGGGCGAGCCCAGAGGGCCCACA
ATCAAGCCCTGTCCTCCATGCAAATGCCCAGCACCTAACCTCTTGGGTGG
ACCATCCGTCTTCATCTTCCCTCCAAAGATCAAGGATGTACTCATGATCT
CCCTGAGCCCCATAGTCACATGTGTGGTGGTGGATGTGAGCGAGGATGAC

-continued

```
CCAGATGTCCAGATCAGCTGGTTTGTGAACAACGTGGAAGTACACACAGC

TCAGACACAAACCCATAGAGAGGATTACAACAGTACTCTCCGGGTGGTCA

GTGCCCTCCCCATCCAGCACCAGGACTGGATGAGTGGCAAGGAGTTCAAA

TGCAAGGTCAACAACAAAGACCTCCCAGCGCCCATCGAGAGAACCATCTC

AAAACCCAAAGGGTCAGTAAGAGCTCCACAGGTATATGTCTTGCCTCCAC

CAGAAGAAGAGATGACTAAGAAACAGGTCACTCTGACCTGCATGGTCACA

GACTTCATGCCTGAAGACATTTACGTGGAGTGGACCAACAACGGGAAAAC

AGAGCTAAACTACAAGAACACTGAACCAGTCCTGGACTCTGATGGTTCTT

ACTTCATGTACAGCAAGCTGAGAGTGGAAAAGAAGAACTGGGTGGAAAGA

AATAGCTACTCCTGTTCAGTGGTCCACGAGGGTCTGCACAATCACCACAC

GACTAAGAGCTTCTCCCGGACTCCGGGTAAATGA.
```

Example 2A

Preparation of an MRFP Construct Including an Fc-Region

The coding sequence for a monomeric form of Ds-Red (mRFP) was PCR amplified using the following primers:

```
                                        (SEQ ID NO: 29)
5'-CGATAAGAAGCTTATGGCCTCCTCCGAGGACGTCATCAAG-3'
and
                                        (SEQ ID NO: 30)
5'-CAAGCTTCGGCGGCCGCGGCGCCGGTGGAGTGG-3'.
```

The product of the PCR reaction was digested with Hind III and Not I to provide cut products. The cut products were gel purified and ligated into the Hind III and Not I cut pCDNA3-Fc plasmid prepared in Example 1. The resulting plasmid expressed a polypeptide with the monomeric Ds-red fluorescence protein variant fused in-frame at the c-terminus to the mouse IgG2a Fc region, separated by a 5 amino acid spacer consisting of AAAGG (SEQ ID NO: 11).

Example 3

Ex-Pressing Constructs with Fluorescent Proteins

Human embryonic kidney cells (HEK) were stably transfected according to the following procedure. HEK cells were grown in DMEM (Biowhittaker), 10% FBS (Hyclone) and 10 µg/ml Ciprofloxacin (Cellgro). Cells were transfected using calcium phosphate transfection with plasmids encoding CFP-Fc, YFP-Fc, paGFP-Fc, or CFP-YFP-Fc. After 24 hours the cell culture medium was supplemented with 1 mg/ml G418 sulfate (Cellgro). 14 days after transfection, cells were positively sorted for high expressors (CFP, YFP, or FRET) using a Becton Dickinson Vantage cell sorter. Clonal cell lines were established by limiting dilution.

A similar procedure was used to prepare cell lines expressing vectors lacking the Fc-region.

Example 4

Preparation of Beads with Immobilized Constructs

Polypeptides including an Fc-region expressed by the cells of Example 3 were immobilized on protein A-coated Sepharose™ beads. The immobilization of constructs lacking an Fc-region to a surface is described first, followed by a description of constructs having an Fc-region.

Example 4A

Immobilizing Constructs Lacking an Fc-Region

Respective cell lines expressing polypeptides including a fluorescent protein and polypeptides including a fusion of two fluorescent proteins were grown to confluency as in Example 3. After extensive washing in phosphate buffered saline, pH 7 (PBS) the cells were lysed in lysis buffer (137 mM NaCl, 20 mM Tris-HCl, pH 7.4, 1 mM EDTA, 0.5% Triton X-100, a mixture of protease inhibitors and 1 mM phenylmethylsulfonyl fluoride). The lysates were centrifuged for 15 minutes at 14,000×g at 4° C.

Supernatant from the centrifuged lysates was precleared with packed protein A-Sepharose (Amersham Biosciences). Protein A coated beads were coated with polyclonal anti-GFP antibody (Molecular Probes). After extensive washing, the beads were incubated with the cleared supernatant from the respective cell lines for 1 hour at 4° C. After 3 washes in lysis buffer, the beads were washed once in 0.2 M triethanolamine, pH 8.2.

The GFP antibody and polypeptide were covalently crosslinked to the beads by resuspending the beads in 0.2 M triethanolamine, pH 8.2 containing 6.6 mg/ml dimethyl pimelimidate (Pierce). The suspension was incubated for 1 hour at room temperature. To quench the reaction, the beads were incubated with 0.1 M ethanolamine, pH 8.2 and allowed to react for 10 minutes at room temperature. After washes in 0.1 M sodium borate, pH 8.5, the beads were stored in 0.1 M sodium borate, 0.1% BSA, 0.05% Tween 20, 0.1% NaN3.

Example 4B

Immobilizing Constructs Having an Fc-Region

Respective cell lines expressing CFP-Fc, GFP-Fc, YFP-Fc, paGFP-Fc, mRFP0Fc, or CFP-YFP-Fc were grown to confluency as in Example 3. After extensive washing in phosphate buffered saline, pH 7 (PBS) the cells were lysed in lysis buffer (137 mM NaCl, 20 mM Tris-HCl, pH 7.4, 1 mM EDTA, 0.5% Triton X-100, a mixture of protease inhibitors and 1 mM phenylmethylsulfonyl fluoride). The lysates were centrifuged for 15 min at 14,000×g at 4° C.

Protein A coated beads (without polyclonal anti-GFP antibody) were incubated with the supernatant from the respective cell lines for 1 hour at 4° C. After 3 washes in lysis buffer, the beads were washed once in 0.2 M triethanolamine, pH 8.2.

The Fc-region of the constructs and protein A were covalently crosslinked by resuspending the beads in 0.2 M triethanolamine, pH 8.2 containing 6.6 mg/ml dimethyl pimelimidate (Pierce). The suspension was incubated for 1 hour at room temperature. To quench the reaction, the beads were incubated with 0.1 M ethanolamine, pH 8.2 and allowed to react for 10 min at room temperature. After washes in 0.1 M sodium borate, pH 8.5, the beads were stored in 0.1 M sodium borate, 0.1% BSA, 0.05% Tween 20, 0.1% NaN3

Example 5

Confocal Imaging of CFP and YFP

Sepharose beads of three types were prepared as in Example 4: (1) beads with an CFP-Fc construct immobilized with respect to the surface of the bead ("CFP beads"), (2) beads with a YFP-Fc construct immobilized with respect to the surface of the bead ("YFP beads"), and (3) beads with a CFP-YFP-Fc construct immobilized with respect to the surface of the bead ("CFP-YFP beads"). Each of these constructs was immobilized with respect to the beads via the Fc-region of the respective construct.

The CFP beads did not include other fluorescent proteins. The YFP beads did not include other fluorescent proteins. The CFP-YFP beads did not include other fluorescent proteins. Excitation of the CFP protein of the CFP-YFP beads resulted in FRET and contributions from FRET donor fluorescence (from CFP of the CFP-YFP-Fc construct) and from FRET acceptor fluorescence (from YFP of the construct).

Referring to FIG. 5, a fluorescence-wavelength plot 300 shows that the CFP, YFP, and CFP-YFP beads exhibited different fluorescence spectra. The fluorescence spectra of the CFP and CFP-YFP beads were obtained by irradiating the beads with argon laser radiation at 405 nm. The fluorescence spectrum of the YFP beads was obtained by irradiating the beads with argon laser radiation at 458 nm. Fluorescence intensities were acquired at 10 nm intervals between 420 nm and 630 nm.

Fluorescence from the CFP beads has a maximum of about 482 nm. Fluorescence from the YFP beads has a maximum of about 530 nm and is negligible below about 490 nm. Fluorescence from the CFP-YFP beads includes features of both CFP bead fluorescence and YFP bead fluorescence. For example, the CFP-YFP bead fluorescence exhibits maxima at both 482 nm and 530 nm.

Beads of each of the three types were combined in a mixture. Confocal images of beads of the mixture were obtained by sequentially scanning an area of the mixture using one laser line per scan. A first scan was performed by irradiating the beads with 458 nm laser radiation. Fluorescence emission between 465 and 495 nm was detected using a CCD detector. A second scan was performed by irradiating the beads with 514 nm laser radiation. Fluorescence emission between 525 and 630 µm was detected.

Referring to FIG. 6a, the first scan detected emission from the CFP protein of the CFP beads and of the CFP-YFP beads by direct excitation of the CFP protein; in the original, the beads appear as green circles. The 458 nm excitation of the CFP-YFP beads also excites some FRET emission by YFP. However, the FRET-induced YFP emission is not seen in FIG. 6a because the detection window between 465 nm and 495 nm excludes most of the FRET emission spectrum (FIG. 5).

Referring to FIG. 6b, the second scan detected emission from the YFP protein of the YFP beads and of CFP-YFP beads by direct excitation of the YFP protein; in the original, the beads appear as red circles. The second scan detected little or no emission from the CFP protein of the CFP beads or of the CFP-YFP beads because the 514 nm irradiation wavelength inefficiently excites the CFP protein. Thus, little or no FRET occurs when the CFP-YFP beads were excited at 514 nm.

The first and second scans of FIGS. 6a and 6b allowed the CFP, YFP, and CFP-YFP beads to be discriminated from one another. For example, a bead 302 appears in the first scan (FIG. 6a), but not in the second scan (FIG. 6b). A bead 304 appears in the second scan, but not in the first scan. Accordingly, bead 302 is a CFP bead whereas bead 304 is a YFP bead. A bead 306 appears in both the first and second scans. Accordingly, bead 306 is a CFP-YFP bead.

Referring to FIG. 6c, an overlay of the first and second scans shows all of the beads present in the individual scans. Although the CFP (medium gray in FIGS. 6a and 6c; green in the original), YFP (dark gray in FIGS. 6b and 6c; red in the original), and CFP-YFP (lightest gray in 6c, yellow in the original) beads can be distinguished from one another, the contribution from FRET emission could not be determined without further analysis.

Example 6

Sensitized Emission Imaging

The sample of Example 5 was imaged by irradiating the beads with 458 nm argon ion laser radiation and detecting emission at 525 nm to 630 nm. Referring to FIG. 7, the contributions of CFP fluorescence (FRET donor fluorescence) and YFP fluorescence were subtracted to provide a corrected image indicative of the amount of FRET emission at each pixel within the image.

Example 7

Acceptor Photobleaching

Referring to FIGS. 8a-8d, a portion (indicated by the square in FIG. 8c) of the sample of Example 5 was repeatedly (100×) irradiated with 514 nm argon laser radiation. The irradiation photobleached YFP present in the irradiated portion. Subsequently, the sample was imaged (FIG. 8a) by irradiating the sample with 458 nm radiation and collecting fluorescence at from 465 nm to 495 nm; the CFP beads appeared as green circles in the original. The sample was then imaged (FIG. 8b) by irradiating the sample with 514 nm radiation and collecting fluorescence at from 525 to 630 nm; the YFP beads appeared as red circles in the original. An overlay of the images of FIGS. 8a and 8b is shown in FIG. 8c; beads appearing in both 8a and 8b (CF-YFP beads) appeared as yellow in the original. The sample was also imaged by irradiating the sample with 458 nm radiation and collecting fluorescence at from 525 to 630 nm (not shown). The portion of the YFP-CFP bead that was irradiated appears as a green arc inside the white box in FIG. 8c. As seen by comparing FIGS. 8b and 8d, the photobleaching eliminated fluorescence from YFP of the YFP constructs and of the CFP-YFP constructs. Consequently, FRET was not observed in the photobleached area.

The three images were used to determine the amount of FRET emission (FIG. 8d). As discussed in Example 5, beads containing CFP (FIG. 8a), YFP (FIG. 8b), and CFP-YFP (FIG. 8d) constructs can be discriminated from one another.

Example 8

Donor Photobleaching

A portion of the sample of Example 5 was repeatedly (100×) irradiated with 458 nm argon laser radiation. The irradiation photobleached both CFP and YFP present in the irradiated portion. Subsequently, the sample was imaged by irradiating the sample with 458 nm radiation and collecting fluorescence at from 465 nm to 495 nm. The sample was imaged by irradiating the sample with 514 nm radiation and collecting fluorescence at from 525 to 630 nm. The sample was also imaged by irradiating the sample with 458 nm radiation and collecting fluorescence at from 525 to 630 nm.

The three images were used to determine the amount of FRET emission. As discussed in Example 5, beads containing CFP, YFP, and CFP-YFP constructs can be discriminated from one another. As seen by comparing the three images, photobleaching eliminated fluorescence from CFP and YFP of the respective CFP and YFP constructs and of the CFP-YFP constructs. Consequently, FRET was not observed in the photobleached area.

Example 9

Fluorescence Lifetime Imaging

Figure 9A:
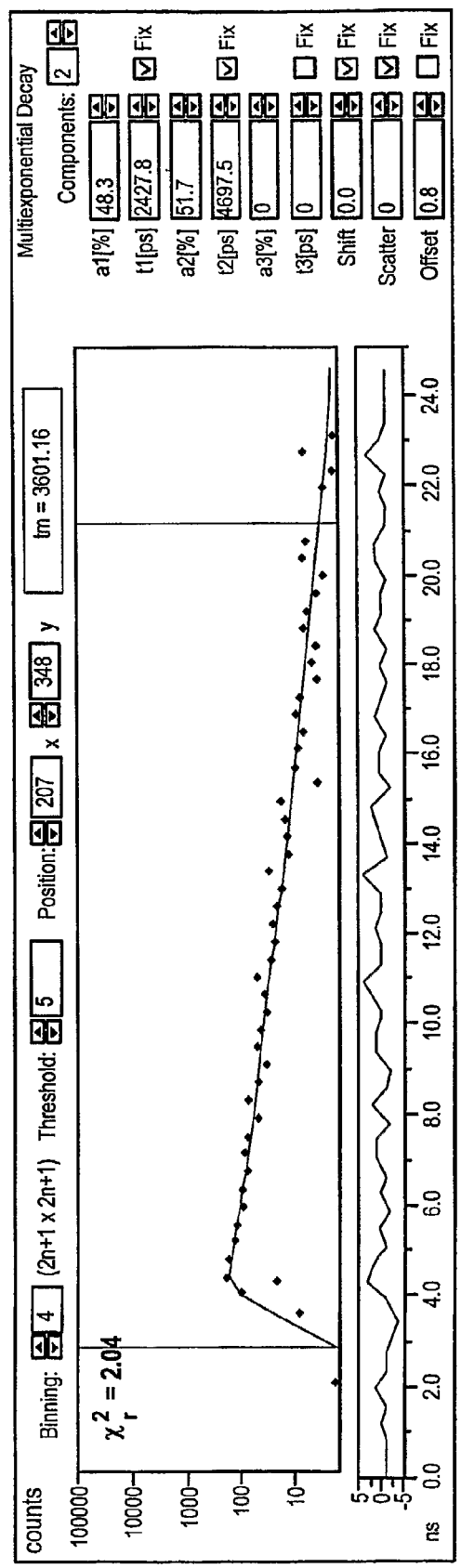
FIG. 9a is a fluorescence decay graph of a bead with cyan immobilized fluorescent protein following excitation with a pulsed laser.

A fluorescence decay curve was obtained by irradiating a bead with immobilized CFP-Fc construct with a 405 nm laser pulse. The results show that the emission decays to about 50% of its maximum value within about 10 ns (see FIG. 9a). This is an example of a CFP lifetime measurement at a single pixel.

A fluorescence intensity image was obtained by irradiating a sample including a mixture of CFP-Fc beads, YFP-Fc beads and CFP-YFP-Fc beads with laser pulses at 405 nm. Shorter lifetimes appear brighter. Note that YFP is not efficiently excited at 405 nm. Thus, YFP-Fc beads appeared only dimly in FIG. 9c.

Figure 9C:
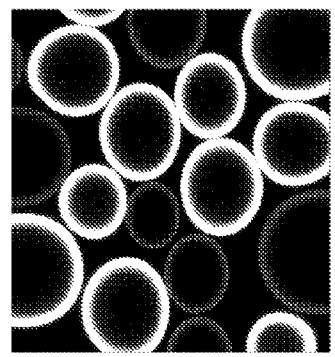
FIG. 9c is an image of the fluorescence lifetimes at different locations within the sample imaged in FIG. 9b. Shorter lifetimes appear brighter.
Figure 9B:
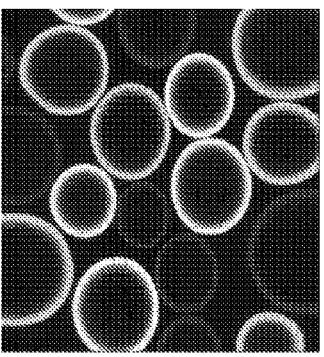
FIG. 9b is an image of the fluorescence intensity observed in a sample including the beads of FIG. 5 upon excitation with a pulsed laser.

The image of FIG. 9b was color coded, with shorter lifetimes appearing with a different color than longer lifetimes. Because FRET shortens the CFP fluorescence lifetime, CFP-YFP-Fc beads are yellow in FIG. 9b while CFP-Fc beads appear green in this particular color coding. Different color codings can be obtained depending on the look-up table used to code for fluorescence lifetimes.

Figure 9D:
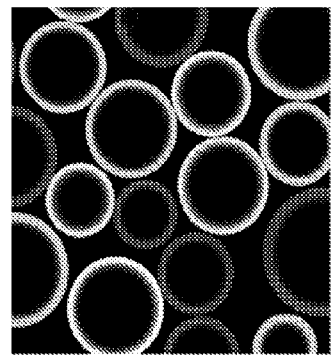
FIG. 9d is an overlay of two images of the sample imaged in FIG. 9b. The first overlay image was obtained by irradiating the beads with 458 nm light and detecting emission between 465 nm and 495 nm. The second overlay image was obtained by irradiating the beads with 514 nm light and detecting emission between 525 and 630 nm. Those beads that are medium gray appeared as green circles in the original; beads that are darkest gray were red in the original; and beads that are lightest gray appear to be yellow in the original

Referring to FIG. 9d, all of the CFP-Fc beads (medium gray, green in original), YFP-Fc beads (darkest gray, red in original) and CFP-YFP-Fc (lightest gray, yellow in original) beads appear in an overlay of a first image obtained with 458 nm steady state excitation and a second image with 514 nm steady state excitation.

Figure 9E:
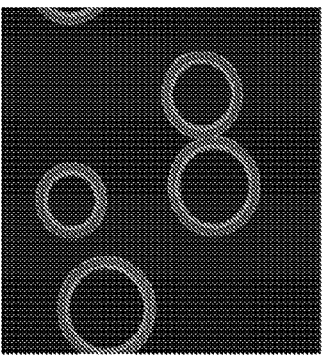
FIG. 9e is an image of FRET emission determined from the image of FIG. 9d and a third image obtained by irradiating the beads with 458 nm light and detecting emission between 525 and 630 nm. The FRET beads appear to be fuchsia with a green penumbra in the original.

Referring to FIG. 9e, the FRET emission determined as described for Example 5 corresponds with the FRET emission determined by lifetime in FIG. 9c. The FRET beads, e.g., the CFP-YFP-Fc beads, appeared a fuchsia circles with a green penumbra.

Example 10

Photoactivation of Photoactivatable GFP (paGFP)

paGFP is a mutant of wtGFP with two excitation peaks (399 nm and 504 nm). The molecule exhibits minimal fluorescence in the non-activated state by illumination at the second peak. After illumination with light exciting the first peak (399 nm), the molecule undergoes a photo-induced conversion that leads to a decrease of absorbance in the first peak (399 nm) and to an increase of absorbance in the second peak (488 nm). This results in enhanced fluorescence intensity of approximately 100-fold. This property can be exploited for the study of protein trafficking over time.

In this example, beads were coated with photoactivatable GFP using methods described herein. Individually selected regions of interest were sequentially activated by irradiation with a 20 mW diode laser emitting at 405 nm. Fluorescence images were obtained with Argon laser (488 nm) excitation. With this technology we were able to highlight small areas on the beads (FIG. 10a-f). From 10a to 10f, different regions of interest have been sequentially photoactivated. The regions that appear light gray were green in the original color image. These results demonstrate that small areas of individual beads can be specifically photoactivated.

Example 11

Use of CFP-Beads and CFP-YFP (FRET) Beads as Standards for the Measurement of Intermolecular Distances by Confocal Microscopic Fluorescent Lifetime Imaging (FLIM)

A pulsed 405 nm laser was used for excitation and photon counting was performed using a 435-485 nm bandpass filter to reject any photon from YFP excitation.

A mixture of beads coated with either CFP-Fc or CFP-YFP-Fc was imaged by fluorescent lifetime imaging. The lifetimes detected at each pixel (512×512) were calculated by a curve-fitting algorithm using biexponential lifetime decays. The lifetime distribution reveals two distinct peaks. The lifetime distribution was then color-coded to produce a lifetime image.

293 cells were stably transfected with Toll-like receptor (TLR) 9 tagged with CFP together with TLR9 tagged with YFP. These cells were incubated with TLR9 activating CpG-DNA at 37 C for 30 minutes. The cells were fixed with paraformaldehyde and imaged by confocal microscopic lifetime imaging. The lifetime image reveals that TLR9 homomultimerizes in endosomal structures in presence of CpG-DNA as the lifetime of CFP is substantially decreased in these areas. FRET efficiency E and intermolecular distances r can be calculated by the following formulas:

FLIM-FRET Efficiency:

$$E = 1 - (r_{DA}/r_D)$$

$r_{DA}$=donor lifetime in presence of acceptor (energy transfer)

$r_D$=donor lifetime in absence of acceptor

Intermolecular Distance:

$$r = R_0 \{(1/E) - 1\}^{1/6}$$

$R_0$ is the distance of separation at which the energy transfer efficiency is 50% (Foerster distance).

The lifetime of a fluorochrome is independent of the concentration. However, if the dye gives away energy (e.g., in FRET) the lifetime decreases, which allows the measurement of FRET lifetime imaging. One measures the lifetime in the presence and in the absence of the acceptor, and if the donor (e.g., CFP in a CFP-YFP pair) gives away energy, the lifetime decrease is recorded and can be quantified.

These results demonstrate that the constructs described herein can be used to detect and quantify lifetime fluorescence as a measure of protein proximity, and the FRET beads (calibration standards) described herein are a useful control for those experiments.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising:
   a plurality of beads having different fluorescence resonance energy transfer (FRET) efficiencies, wherein immobilized on each of the beads are fusion proteins comprising:
      first and second fluorescent proteins, wherein the first and second fluorescent proteins are a FRET pair;
      a linker of a known length between the first and second fluorescent proteins; and
      an Fc region linked to one of the fluorescent proteins,
   the plurality of beads comprising fusion proteins with linkers of varied lengths to produce the different FRET efficiencies,
   wherein each bead comprises a marker so that beads with different FRET efficiencies can be identified in a mixture.

2. The composition of claim 1, wherein at least one of the first and second fluorescent proteins is a green fluorescent protein or variant thereof.

3. The composition of claim 2, wherein the green fluorescent protein or variant thereof is selected from the group consisting of green fluorescent protein (GFP), cyan fluorescent protein (CFP), photoactivatable green fluorescent protein (paGFP), and yellow fluorescent protein (YFP).

4. The composition of claim 1, wherein at least one of the first and second fluorescent proteins is a reef coral fluorescent protein (RCFP) or variant thereof.

5. The composition of claim 4, wherein the fluorescent protein is selected from *Anemonia majano* cyan fluorescent protein (AmCyan), *Zoanthus* sp. green fluorescent protein (ZsGreen), *Zoanthus* sp. yellow fluorescent protein (ZsYellow), *Discosoma* sp red fluorescent protein (DsRed), *Anemonia sulcata* fluorescent protein (AsRed), and *Heteractis crispa* red fluorescent protein (HcRed).

6. The composition of claim 1, wherein the Fc-region is derived from mouse immunoglobulin.

7. The composition of claim 1, wherein the linker is an enzyme-cleavable linker.

8. The composition of claim 7, wherein the enzyme that cleaves the linker is a protease.

9. The composition of claim 1, wherein the FRET pair comprises one of CFP-YFP, GFP-mRFP1, YFP-mRFP1, or GFP-RFP.

10. The composition of claim 1, wherein at least some of the linkers have a length of 10 nm or less.

11. A FRET method, the method comprising:
    obtaining the composition of claim 1;
    irradiating the composition with light having a wavelength and intensity sufficient to excite detectable fluorescence and FRET emission from one or both of the first and second fluorescent proteins; and
    obtaining a first fluorescence signal from at least one of the first or second fluorescent proteins.

12. The composition of claim 1, wherein the marker is a fluorophore with a characteristic emission spectrum.

13. The composition of claim 12, wherein the fluorophore with a characteristic emission spectrum is one of the first or second fluorescent proteins.

* * * * *